United States Patent
Notohara et al.

(10) Patent No.: US 9,763,632 B2
(45) Date of Patent: Sep. 19, 2017

(54) RADIOGRAPHIC APPARATUS AND METHOD OF USING THE SAME

(71) Applicant: Shimadzu Corporation, Kyoto-shi (JP)

(72) Inventors: Daisuke Notohara, Kyoto (JP); Junpei Sakaguchi, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 385 days.

(21) Appl. No.: 14/521,467

(22) Filed: Oct. 23, 2014

(65) Prior Publication Data

US 2016/0113601 A1   Apr. 28, 2016

(51) Int. Cl.
*A61B 6/00* (2006.01)
*A61B 6/02* (2006.01)
*A61B 6/06* (2006.01)

(52) U.S. Cl.
CPC ............ *A61B 6/4035* (2013.01); *A61B 6/025* (2013.01); *A61B 6/06* (2013.01); *A61B 6/4476* (2013.01); *A61B 6/5205* (2013.01)

(58) Field of Classification Search
CPC .................................................. A61B 6/4035
See application file for complete search history.

(56) References Cited

U.S. PATENT DOCUMENTS

| | | | |
|---|---|---|---|
| 7,680,249 B2 * | 3/2010 | Yuan | A61B 6/00 378/156 |
| 2009/0122952 A1 * | 5/2009 | Nishide | A61B 6/032 378/4 |
| 2011/0058649 A1 | 3/2011 | Wear et al. | |
| 2011/0075810 A1 * | 3/2011 | Sendai | A61B 6/4042 378/95 |

FOREIGN PATENT DOCUMENTS

JP    04-141156    5/1992

* cited by examiner

*Primary Examiner* — Dani Fox
(74) *Attorney, Agent, or Firm* — Muir Patent Law, PLLC

(57) ABSTRACT

A radiographic apparatus and method of obtaining images using a radiographic apparatus are disclosed. The radiographic apparatus and method use a filter having different regions for different radiation states. The filter is configured to be moved during different irradiating radiation steps. The radiation from the different steps is detected and may be used to generate an image.

20 Claims, 14 Drawing Sheets

RADIOGRAPHIC APPARATUS AND METHOD OF USING THE SAME

BACKGROUND

The present disclosure relates to a radiographic apparatus for taking an image by irradiating radiation to a subject, and more specifically to a radiographic apparatus in which a radiation source moves with respect to a subject during the image taking operation.

DESCRIPTION OF THE RELATED ART

The following description of the related art sets forth the inventors' knowledge of related art and certain features therein and should not be construed as an admission of knowledge in the prior art.

In medical institutions, as shown in FIG. 24, a radiation tomography apparatus 51 for obtaining a tomographic image of a subject may be used. In some radiation tomography apparatuses 51 of this kind, the apparatus is configured to obtain a tomographic image by superimposing a series of transparent images consecutively taken while synchronously moving a radiation source 53 for irradiating radiation and a FPD 54 for detecting the radiation. In such a radiation tomography apparatus 51, during the image taking operation of a series of transparent images, the radiation source 53 and the FPD 54 move so as to approach with each other in a body axis direction of the subject. After the position of the radiation source 53 and that of the FPD 54 in the body axis direction coincide, the radiation source 53 and the FPD 54 move so as to distance themselves with respect to each other in the body axis direction.

The operation of taking a tomographic image mentioned above by the radiation tomography apparatus 51 will be explained. Initially, the radiation source 53 irradiates radiation intermittently while moving. For example, every time one irradiation is completed, the radiation source 53 moves in the body axis direction of the subject and again irradiates radiation. Thus, several pieces (e.g., 74) of transparent images are taken, and reconstructed into a tomographic image by a filter back projection method. The completed tomographic image is an image in which a tomogram taken by cutting the subject at a certain cutting plane is seen.

Some radiation tomography apparatuses 51 can acquire a subtraction image in which soft tissues and/or bony parts of a subject are emphasized by obtaining a difference of two images obtained by performing two kinds of image taking operations. The operation for taking a subtraction image in a conventional radiation tomography apparatus 51 will be explained.

In a conventional radiation tomography apparatus, as shown in FIG. 25, while alternately performing an image taking operation in which the radiation source 53 is set to a high voltage state and an image taking operation in which the radiation source 53 is set to a low voltage state, the radiation source 53 and the FPD 54 are moved with respect to the object. With this, a transparent image under the high voltage condition and a transparent image under the low voltage condition are taken alternately. After the image taking operations, if a tomographic image is reconstructed only from the transparent images taken by the high voltage image taking operations, a tomographic image under the high voltage condition can be obtained. Further, if a tomographic image is reconstructed only from the transparent images taken by the low voltage image taking operations, a tomographic image under the low voltage condition can be obtained. At this time, the radiation source 53 moves always in the same direction during the image taking operation.

Comparing tomographic images different in image taking condition, the subject images seen therein are different. Concretely, the contrast difference between the soft tissue and the bony part of the subject seen in the tomographic image under the high voltage condition differs from the contrast difference between the soft tissue and the bony part of the subject seen in the tomographic image under the low voltage condition. Therefore, by subtracting the tomographic image taken under the high voltage condition from the tomographic image taken under the low voltage condition, both the images are not simply balanced out, but, for example, the soft tissue of the subject is more emphasized or the bony part of the subject is emphasized. In a conventional radiation tomography apparatus 51, a subtraction image emphasized in soft tissues or bony parts of a subject is obtained using the above.

In some conventional radiation tomography apparatuses 51, a filter 53f for changing the radiation quality of the radiation source 53 is provided (see FIG. 24). This filter 53f is constituted by a gadolinium filter for high voltage irradiation and a copper filter for low voltage irradiation. The gadolinium filter and the copper filter are switched by operating a controller (see, for example, JP H04-141156, A, incorporated herein in its entirety by reference).

However, in a conventional radiation tomography apparatus, there may be certain problems. For example, in a conventional radiation tomography apparatus, an image taking method cannot typically be changed flexibly. For example, a subtract tomography function cannot be simply added to a general-purpose radiographic apparatus. The filter 53f should be arranged adjacent to the radiation source 53. This reason will be explained below. The radiation beam irradiated form the radiation source 53 reaches the subject M while being expanded radially. Therefore, the width of the radiation beam immediately after irradiated form the radiation source 53 is narrow. As the radiation beam distances from the radiation source 53, the beam width increases. In order for the radiation beam irradiated from the radiation source 53 to assuredly pass through the filter 53f, the beam should be transmitted through the filter 53f while the beam width is narrow. As such, the filter 53f should be provided adjacent to the radiation source 53.

Therefore, the filter 53f is required to be provided at the position in between the radiation source 53 and a collimator. A collimator denotes a movable slit for adjusting the expanse of the radiation beam irradiated form the radiation source 53. That is, the radiation beam passes through the filter 53f and then passes through the collimator. On the other hand, if it is set such that the radiation beam passes through the collimator and the filter 53f in this order, a considerably large filter 53f may be required because the radiation beam passed through the filter 53f has considerably increased in width. Such setting is not particularly realistic.

The restriction of the installation position of the filter 53f as mentioned above may cause the following problems. For example, if it is attempted to use a general-purpose radiographic apparatus to take a subtraction tomographic image, a major alternation will be required. In order to enable to take a subtraction tomographic image, a filter 53f may be used. This filter 53f should be arranged between the radiation source 53 and the collimator as mentioned above. A general-purpose radiographic apparatus, however, is in a situation in which a collimator has been already installed on a radiation source 53. Therefore, in order to enable to take a subtraction tomographic image, it may be necessary to alter the apparatus such that the collimator is detached from the radiation source 53 and that a filter 53f is attached and then the collimator is attached to the radiation source.

Once the filter 53f is attached, the radiographic apparatus becomes an apparatus dedicated to take a subtraction image. If it is attempted to perform a normal image taking operation such as a spot image taking operation, the filter 53f should be removed from the apparatus. Even so, if a general image taking operation is performed in a state in which the filter 53f is attached, the radiation passes through the filter 53f, changing the radiation quality of the radiation, which prevents a prescribed image taking operation. In performing an image taking operation, there are various image taking methods. There are some cases in which it is desired to change image taking methods arbitrarily in the course of image taking operations. In such a case, it cannot be said that a conventional apparatus that requires major alternations is the most suitable structure in use.

The description herein of advantages and disadvantages of various features, embodiments, methods, and apparatuses disclosed in other publications is in no way intended to limit the present invention. For example, certain features of the described embodiments of the invention may be capable of overcoming certain disadvantages and/or providing certain advantages, such as, e.g., disadvantages and/or advantages discussed herein, while retaining some or all of the features, embodiments, methods, and apparatus disclosed therein.

SUMMARY

The various disclosed embodiments have been made in view of the aforementioned circumstances, and aim to provide a radiographic apparatus capable of taking a subtraction tomographic image and changing image taking methods.

Some embodiments have the following structure. For example, the radiographic apparatus according to one embodiment may include: a radiation source that irradiates radiation toward a subject; radiation source control means for controlling a voltage of the radiation source; radiation source moving means for moving the radiation source with respect to the subject; a radiation source movement control means for controlling the radiation source moving means; a filter having a high voltage region through which the radiation irradiated when the radiation source is in a high voltage state passes and a low voltage region through which the radiation irradiated when the radiation source is in a low voltage state passes; a holder that moves in accordance with a movement of the radiation source and holds the filter; holder rotation means for rotating the holder; holder rotation control means for controlling the holder rotation means; radiation detection means for detecting the radiation passed through the filter and the subject; and image generation means for generating an image based on an output of the radiation detection means.

In one embodiment, in a radiographic apparatus in which a radiation source moves with respect to a subject, it can be structured to generate a subtraction image by obtaining a difference between an image taken in a high voltage state and an image taken in a low voltage state. According to the structure, by rotating the holder, it is possible to select whether or not the radiation irradiated from the radiation source should pass through the filter for taking a subtraction image. For example, after performing the image taking operation in a state in which radiation passes through the filter for taking a subtraction image, if it is desired to perform an image taking operation in a state in which the radiation does not pass through the filter, by rotating the holder, the image taking operation can be immediately performed in a continued manner. This is because that the apparatus can cope with the changing of image taking methods by simply rotating the holder between image taking operations. Although the apparatus is an apparatus capable of taking a subtraction image, an image taking operation other than a subtraction image taking operation can be performed immediately. Accordingly, a radiographic apparatus capable of flexibly performing image taking operations can be provided.

Further, in the aforementioned radiographic apparatus, it may be desirable that the holder rotation means selects whether or not the radiation irradiated from the radiation source should pass through the filter, and moves the high voltage region of the filter to the position where the radiation passes through when the radiation source is in a high voltage state and the low voltage region of the filter to the position where the radiation passes through when the radiation source is in a low voltage state.

The aforementioned structure shows a concrete structure of a radiographic apparatus. If it is configured such that the holder rotation means changes the radiation passing position in the filter in accordance with the voltage of the radiation source, an image taking operation can be performed assuredly with an appropriate exposure.

Further, in the aforementioned radiographic apparatus, it may be desirable to configure such that, after moving one of regions of the filter to a position where the radiation passes through, when the holder rotation means moves the other region to the position where the radiation passes through, the holder rotation means inverts the rotational direction of the holder.

Like the aforementioned structure, after moving one of the regions of the filter to a position where the radiation passes through, if the rotational direction of the holder is reversed when the other region is moved to a position where the radiation passes through, it becomes possible to take a subtraction image simply by slightly moving the filter.

Further, in the aforementioned radiographic apparatus, it may be desirable that the filter is a filter for taking a subtraction image, and the radiographic apparatus further includes: image subtraction means for generating a subtraction image by obtaining a difference between an image continuously taken under a high voltage condition of the radiation source and an image continuously taken under a low voltage condition of the radiation source; and image composing means for generating a composite image by composing the subtraction images.

The aforementioned structure concretely shows a structure that can be used for taking a subtraction image in the radiographic apparatus.

Further, in the aforementioned radiographic apparatus, it may be desirable that the holder holds a filter used except for a purpose of taking a subtraction image, and the holder rotation means rotates the holder to change a type of the filter through which the radiation passes.

The aforementioned structure shows a concrete structure of the radiographic apparatus of the present disclosed embodiments. For example, if it is configured such that the type of filters through which radiation passes can be changed by rotating the holder, changing of filters can be performed depending on the purpose of the image taking operation. For example, when performing a spot image taking operation, the operation can be performed by selecting a filter appropriate to the image taking operation.

Further, in the aforementioned radiographic apparatus, it may be desirable that the apparatus further includes a collimator that limits an irradiation range of the radiation passed through the holder.

The aforementioned structure shows a concrete structure of the radiographic apparatus. By providing a collimator that limits an irradiation range of the radiation passed through the holder, the holder is naturally positioned in between the radiation source and the collimator. With this, the filter provided at the holder and the radiation source can be arranged adjacently. Thus, the size of the filter can be reduced. This is because the radiation irradiated from the radiation source is smallest in width immediately after irradiation.

Further, in the aforementioned radiographic apparatus, it may be desirable that the apparatus further includes: detector moving means for moving the radiation detection means with respect to the subject; and detector movement control means for controlling the detector moving means, wherein when the radiation source is moved, the radiation detection means is moved with respect to the subject.

The aforementioned structure shows a concrete structure of the radiographic apparatus. According to the aforementioned structure, it is possible to move the radiation detection means with respect to the subject. With this, a radiographic apparatus capable of coping with more various kinds of image taking styles can be provided.

Further, in the aforementioned radiographic apparatus, it may be desirable that the image reconstruction means generates a tomographic image obtained by cutting the subject M with a virtual plane as a composite image.

The aforementioned structure shows a concrete structure of the radiographic apparatus. That is, according to the aforementioned structure, a tomographic image can be generated. The movement of the radiation source and that of the radiation detection means are opposite in direction.

Further, in the aforementioned radiographic apparatus, it may be desirable that the image composing means arranges elongated subtraction images extending in a direction perpendicular to a moving direction of the radiation source and joins them to thereby generate the composite image.

The aforementioned structure shows a concrete structure of the radiographic apparatus. For example, according to the aforementioned structure, it is configured such that an intermediate image taken by a slot image taking operation is taken and a tomographic image is obtained from this. By performing such an image taking operation, a radiographic apparatus capable of obtaining a tomographic image taken in a wide range can be provided.

Further, in the aforementioned radiographic apparatus, it may be desirable that the image composing means divides the subtraction image into elongated strip-like images extending in a direction perpendicular to a moving direction of the radiation source and joins the strip-like images the same in an irradiation direction of radiation to generate an intermediate image and generate a tomographic image to be obtained by cutting the subject with a virtual plane from the intermediate image as the composite image.

The aforementioned structure shows a concrete structure of the radiographic apparatus. For example, according to the aforementioned structure, it is configured such that an intermediate image taken by a slot image taking operation is taken and a tomographic image is obtained from this. By performing such an image taking operation, a radiographic apparatus capable of obtaining a tomographic image taken in a wide range can be provided.

Further, in the aforementioned radiographic apparatus, it may be desirable that the composite image generated by the image composing means is an image formed by arranging elongated subtraction images extending in a direction perpendicular to a moving direction of the radiation source in the moving direction of the radiation source and joining them, and the radiation detection means does not move with respect to the subject during the image taking operation.

The aforementioned structure shows a concrete structure of the radiographic apparatus. For example, according to the aforementioned structure, it shows a structure that the radiation detection means does not move during the image taking operation. With this, a radiographic apparatus more simplified in control can be provided.

According to the structure, by rotating the holder, it is possible to change whether or not the radiation irradiated from the radiation source passes through a filter for taking a subtraction image. As such, after performing an image taking operation in a state in which radiation passes through the filter for taking a subtraction image, if it is desired to perform an image taking operation in a state in which the radiation does not pass through the filter, by rotating the holder, the image taking operation can be immediately continued. Accordingly, a radiographic apparatus capable of flexibly performing an image taking operation can be provided.

According to certain embodiments, a method of obtaining images using a radiographic apparatus is disclosed. The radiographic apparatus includes a radiation source, a filter including first and second regions, and a radiation detector. The method includes: controlling a voltage used by the radiation source for irradiation; controlling movement of the radiation source with respect to the subject; irradiating radiation using the radiation source in one of a high voltage state or a law voltage state through the first region of the filter; detecting, by the radiation detector, the radiation passed through the first region of the filter and the subject; moving the filter; after moving the filter, irradiating radiation using the radiation source in the other of the high voltage state or the low voltage state through the second region of the filter; detecting, by the radiation detector, the radiation passed through the second region of the filter and the subject; and generating an image based on output from the radiation detector.

The above and/or other aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/ or advantages of particular embodiments should not be construed as limiting other embodiments or the claims.

In the drawings, the size and relative sizes of layers and regions may be exaggerated for clarity. Like numbers refer to like elements throughout. The terminology used herein is for the purpose of describing particular embodiments only and is not intended to be limiting of the invention. As used herein, the singular forms "a", "an" and "the" are intended to include the plural forms as well, unless the context clearly indicates otherwise. As used herein, the term "and/or" includes any and all combinations of one or more of the associated listed items and may be abbreviated as "/". It will be understood that, although the terms first, second, etc. may be used herein to describe various elements, these elements should not be limited by these terms. Unless indicated otherwise, these terms are only used to distinguish one element from another. For example, a first object could be termed a second object, and, similarly, a second object could be termed a first object without departing from the teachings of the disclosure.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. It will be understood that when an element is referred to as being "connected" or "coupled" to or "on" another element, it can be directly connected or coupled to or on the other element or intervening elements may be present. In contrast, when an element is referred to as being "directly connected" or "directly coupled" to another element, there are no intervening elements present.

Other words used to describe the relationship between elements should be interpreted in a like fashion (e.g., "between" versus "directly between," "adjacent" versus "directly adjacent," etc.). However, the term "contact," as used herein refers to direct contact (i.e., touching) unless the context indicates otherwise.

Terms such as "same," "planar," or "coplanar," as used herein when referring to orientation, layout, location, shapes, sizes, amounts, or other measures do not necessarily mean an exactly identical orientation, layout, location, shape, size, amount, or other measure, but are intended to encompass nearly identical orientation, layout, location, shapes, sizes, amounts, or other measures within acceptable variations that may occur, for example, due to manufacturing processes. The term "substantially" may be used herein to reflect this meaning.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein.

BRIEF DESCRIPTION OF THE DRAWINGS

The disclosed embodiments of the present invention are shown by way of example, and not limitation, in the accompanying figures.

DETAILED DESCRIPTION OF EMBODIMENTS

Figure 1:
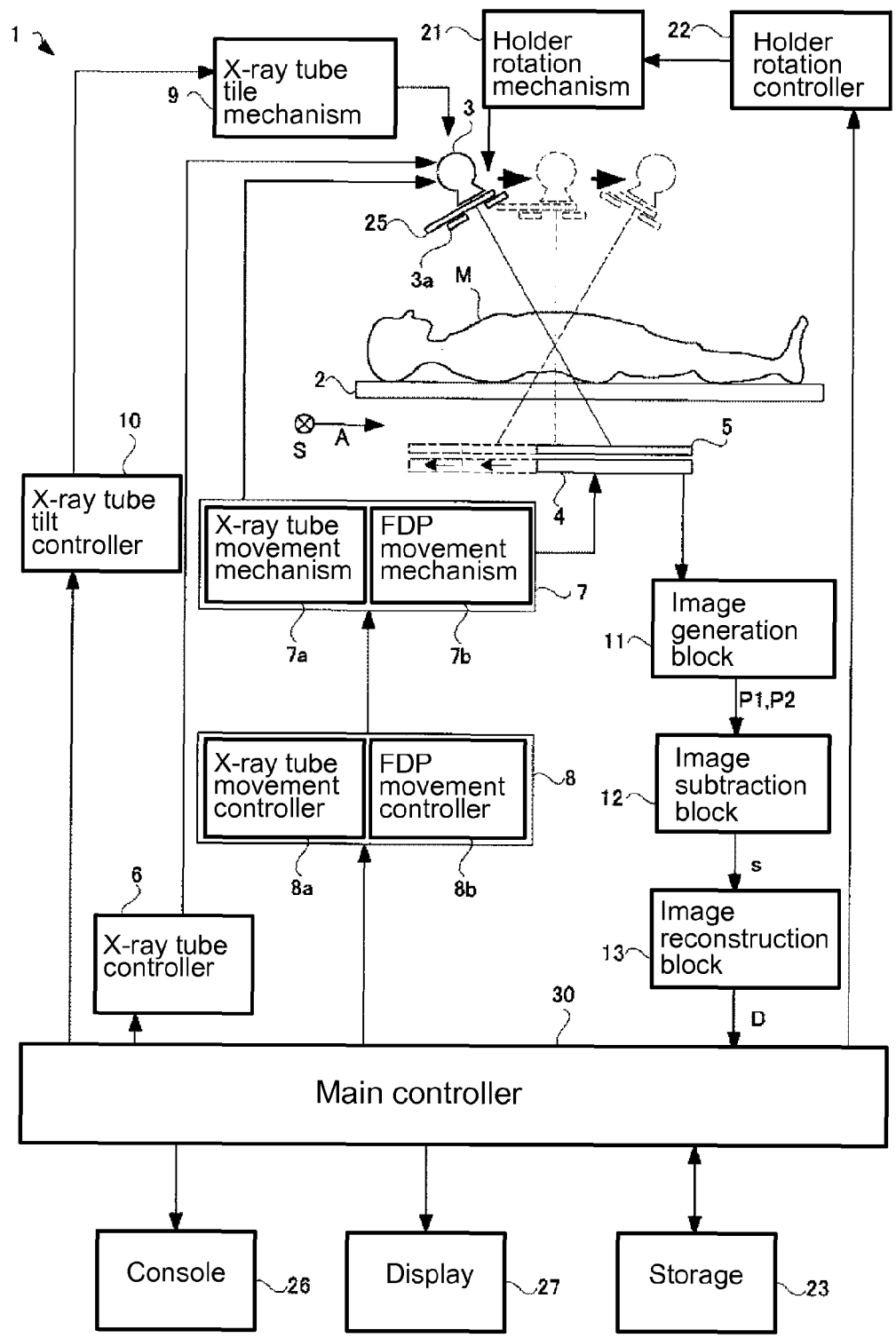
FIG. 1 is a functional block diagram explaining an entire structure of a radiographic apparatus according to Embodiment 1.

In the following paragraphs, some embodiments of the invention will be described by way of example and not limitation. It should be understood based on this disclosure that various other modifications can be made by those in the art based on these illustrated embodiments.

Embodiment 1

Embodiments of a radiation tomography apparatus according to certain examples will be explained with reference to the attached drawings. The X-ray as recited in this disclosure corresponds to radiation as defined in the present invention. The FPD is an abbreviation of a flat-panel type X-ray detector.

The various "sections" or "blocks" described herein may be implemented as devices formed of different elements configured to perform the described actions. For example, each of the blocks, such as the image generation block 11, image subtraction block 12, etc., may be formed of a combination of hardware with software and/or firmware. A block may be configured to perform certain actions by using or programming different circuitry, hardware, software, firmware, or combinations thereof. Various of the blocks may be formed similarly, and certain blocks/sections may be physically combined, for example, to be implemented with the same hardware and/or firmware, having different software programs or algorithms to perform different tasks. Similarly, the "controllers" described herein may be implemented using hardware, software, and/or firmware configured to perform the various actions described herein. Further, although certain controllers may be described separately, certain described controllers may perform actions in concordance with other controllers, such that combinations of controllers may be referred to as a single "controller."

In general, the image generation block 11, image subtraction block 12, image reconstruction block 13, and other elements of image processing apparatus may be comprised of one or more processors or computers configured by software. Other elements of radiographic equipment 1, described further below, such as a main controller 30, console, 26, display 27, and storage 23 may constitute elements of such computer(s). A "computer" refers to one or more apparatus and/or one or more systems that are capable of accepting a structured input, processing the structured input according to prescribed rules, and producing results of the processing as output.

Examples of a computer may include: a general purpose computer; a stationary and/or portable computer; a computer having a single processor, multiple processors, or multi-core processors, which may operate in parallel and/or not in parallel; a supercomputer; a mainframe; a super mini-computer; a mini-computer; a workstation; a micro-computer; a server; a client; a telecommunications device with internet access; a tablet personal computer (PC); a personal digital assistant (PDA); application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, or a chip set; a system on a chip (SoC), or a multiprocessor system-on-chip (MPSoC).

"Software" refers to prescribed rules to operate a computer. Examples of software may include: code segments; instructions; applets; pre-compiled code; compiled code; interpreted code; computer programs; and programmed logic. A computer as described herein may include software in order to perform particular actions.

FIG. 1 is a functional block diagram explaining the structure of a radiographic apparatus according to Embodiment 1. As shown in FIG. 1, the X-ray equipment 1 according to Embodiment 1 is provided with a top board 2, an X-ray tube 3, an FPD 4, a synchronous movement mechanism 7, a synchronous movement controller 8, and an X-ray grid 5. The top board 2 is configured to place a subject M, which is an object of the X-ray tomography, thereon. The X-ray tube 3 irradiates a corn-shaped X-ray beam to the subject M arranged on the upper portion of the top board 2 (one surface side of the top board 2). The FPD 4 is arranged below the top board 2 (on the other surface side of the top board) to detect a transparent X-ray image of the subject M. The synchronous movement mechanism 7 is configured to move the X-ray tube 3 and the FPD 4 synchronously in opposite directions with respect to the part of interest of the subject M in a state in which, in one embodiment, the central axis of the corn-shaped X-ray beam and the central point of the FPD 4 always coincide. The synchronous movement controller 8 controls the synchronous movement mechanism 7. The X-ray grid 5 is arranged so as to cover the X-ray detection plane for detecting the X-ray of the FPD 4 to absorb the scattered X-rays. As explained above, the top board 2 is arranged at the position between the X-ray tube 3 and the FPD 4. The FPD 4 detects the X-ray passed through the filter 25f and the subject M. The X-ray tube 3 corresponds to a radiation source of the present disclosed embodiments, and the FPD 4 corresponds to a radiation detector of the present disclosed embodiments.

The synchronous movement mechanism 7 is provided with an X-ray tube movement mechanism 7a that moves the X-ray tube 3 in the body axis direction A with respect to the subject M, and an FPD movement mechanism 7b that moves the FPD 4 in the body axis direction A with respect to the subject M. The synchronous movement controller 8 is provided with an X-ray tube movement controller 8a for controlling the X-ray tube movement mechanism 7a and an FPD movement controller 8b for controlling the FPD movement mechanism 7b. The X-ray tube corresponds to the radiation source moving means of the present disclosure, and the X-ray tube movement controller 8a corresponds to the radiation source movement control means of the present disclosure, also described herein as a radiation source movement controller.

The X-ray tube 3 is configured to repeatedly irradiate corn-shaped pulsed X-ray beams to the subject M in accordance with the control of the X-ray tube controller 6. The X-ray tube 3 is equipped with a collimator 3a that collimates the X-ray beam into a pyramid corn-shape. The X-ray tube 3 and the FPD 4 constitute an imaging system 3 and 4 for taking an X-ray transparent image. By controlling the voltage of the X-ray tube 3, the X-ray tube controller 6 can make the X-ray tube 3 irradiate an X-ray by applying a high voltage to the X-ray tube 3 or can make the X-ray tube 3 irradiate an X-ray by applying a low voltage to the X-ray tube 3. The X-ray tube controller 6, also described as a radiation source irradiation controller, corresponds to the radiation source control means of the present disclosure. The radiation source movement controller and radiation source irradiation controller may be described together herein as a radiation source controller.

The synchronous movement mechanism 7 is configured to synchronously move the X-ray tube 3 and the FPD 4 with respect to the subject M. This synchronous movement mechanism 7 moves the X-ray tube 3 straight along the straight line orbit (in the longitudinal direction of the top board 2) parallel to the body axis direction A of the subject M in accordance with the control of the synchronous movement controller 8. The moving directions of the X-ray tube 3 and the FPD 4 coincide with the longitudinal direction of the top board 2. Further, during the examination, in certain embodiments, the corn-shaped X-ray beam irradiated from the X-ray tube 3 is always pointed to the part of interest of the subject M, and the X-ray irradiation angle can be changed, for example, from an initial angle of −20° to a final angle of +20° by changing the angle of the X-ray tube 3. Such X-ray irradiation angle change is performed by an X-ray tube tilt mechanism 9. The X-ray tube tilt controller 10 is provided for the purpose of controlling the X-ray tube tilt mechanism 9.

Further, the X-ray equipment 1 according to Embodiment 1 is provided with a main controller 30 for generally controlling each controller 6, 8, 10, 18b, and 22, and a display 27 for displaying a tomographic image D. This main controller 30 may be constituted by a CPU and executes various kinds of programs to realize each controller 6, 8, 10, 18b and 22 and the below-mentioned each portion 11, 12, and 13. In one embodiment, the storage 23 stores all of data related to the control of the X-ray equipment 1, such as parameters related to the control of the X-ray tube 3. The console 26 is used to input each operation by the operator to the X-ray equipment 1.

Further, the synchronous movement mechanism 7 moves the FPD 4 arranged below the top board 2 straight in the body axis direction A (the longitudinal direction of the top board 2) of the subject M in synchronization with the straight movement of the X-ray tube 3. The moving direction is opposite to the moving direction of the X-ray tube 3. In other words, it is structured such that the corn-shaped X-ray beam in which the focal position and irradiation direction of the X-ray tube 3 changes in accordance with the movement of the X-ray tube 3 is always received by the entire surface of the X-ray detection plane of the FPD 4. As explained above, during a single examination, the FPD 4 acquires a total of, for example, 74 pieces of transparent images while moving in synchronization with the X-ray tube 3 in a direction opposite to the moving direction of the X-ray tube 3. Specifically, the imaging system 3 and 4 moves from the initial position shown by an actual line to the position shown by an alternate long and short dash line via the position shown by a broken line as shown in FIG. 1. Thus, a plurality of X-ray transparent images are taken while changing the position of the X-ray tube 3 and that of the FPD 4. In certain embodiments, the corn-shaped X-ray beam is always received by the entire surface of the X-ray detection plane of the FPD 4, and therefore the central axis of the corn-shaped X-ray beam always coincides with the center point of the FPD 4 during the image taking operation. Further, during the image taking operation, although the center of the FPD 4 moves straight, the direction of the movement is opposite to the direction of the movement of the X-ray tube 3. As such, it is structured such that the X-ray tube 3 and the FPD 4 are synchronously moved along the body axis direction A in opposite directions with each other.

Further, at the following stage of the FPD 4, an image generation block/section 11 for generating a transparent image based on a detection signal output from the FPD 4 is provided. At the further following stage of the image generation block/section 11, an image subtraction block/section 12 for generating subtraction images s by obtaining a difference between transparent images P1 continuously taken under a high voltage condition of the X-ray tube 3 and transparent images P2 continuously taken under a low voltage condition of the X-ray tube 3, and an image reconstruction block/section 13 for generating a tomographic image D by composing subtraction images s. The image generation block/section 11 corresponds to image generation means of the present disclosure. The image subtraction block/section 12 corresponds to image subtraction means of the present disclosure, and the image reconstruction block/section 13 corresponds to image composing means of the present disclosure. As described previously, the different blocks/sections described herein may be implemented using hardware, software, and/or firmware, such as certain processors, memory, circuitry, and computer programs, for example, configured to carry out the image processing described herein.

Figure 2:
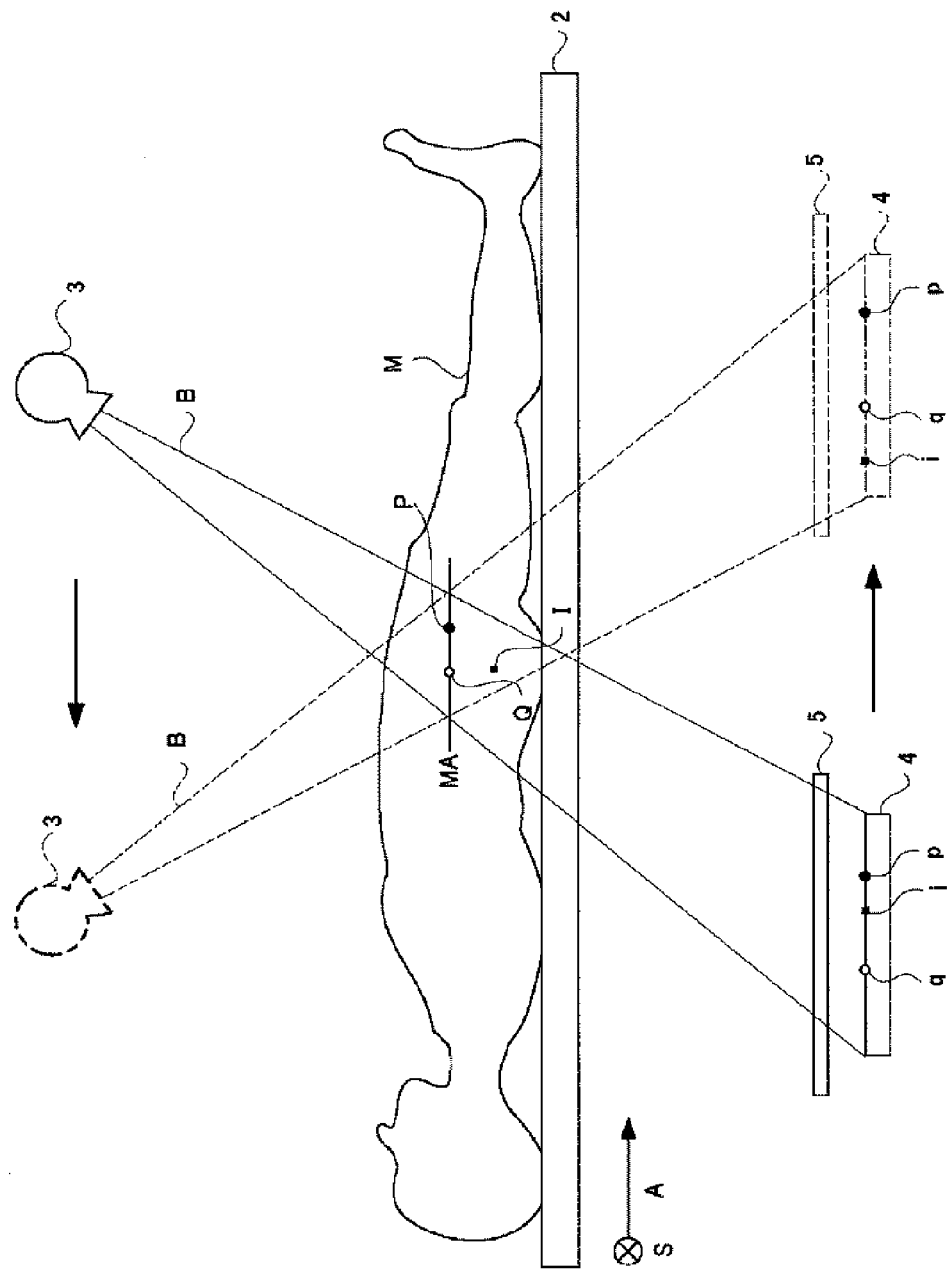
FIG. 2 is a schematic view explaining an image taking principle of the radiographic apparatus according to Embodiment 1.

Next, the principle of obtaining a tomographic image of the X-ray equipment 1 according to Embodiment 1 will be explained. FIG. 2 is a view explaining the method of obtaining a tomographic image by the X-ray equipment according to Embodiment 1. For example, the explanation will be directed to a virtual plane (reference cutting plane MA) parallel to the top board 2 (horizontal with respect to the vertical direction). As shown in FIG. 2, a series of transparent images P are generated in the image generation block/section 11 while synchronously moving the FPD 4 in a direction opposite to the moving direction of the X-ray tube 3 in line with the irradiation direction of the corn-shaped X-ray beam B by the X-ray tube 3 so that the points P and Q positioned on the reference cutting plane MA are always projected to the fixed points p and q on the X-ray detection plane, respectively. In the series of transparent images P1 and P2, the projection image of the subject M is seen while changing its position. By restructuring the series of transparent images P1 and P2 at the image reconstruction block/section 13, the images (e.g., fixed points p, q) positioned on the reference cutting plane MA are integrated, enabling imaging as an X-ray tomographic image. On the other hand, the point I not positioned on the reference cutting plane MA is seen as a point i in each of the series of subject images while changing its projection position on the FPD 4. Such point i, different from the fixed points p and q, does not focus into an image at the time of superimposing the X-ray transparent images at the image reconstruction block/section 13, and blurs. As explained above, by superimposing the series of transparent images, an X-ray tomographic image in which only the image positioned at the reference cutting plane MA of the subject M is seen can be obtained. As explained above, by simply superimposing the X-ray transparent images, a tomographic image D at the reference cutting plane MA can be obtained.

Further, by changing the setting of the image reconstruction block/section 13, even at any arbitrary cutting plane horizontal to the reference cutting plane MA, a similar tomographic image can be obtained. During the image taking operation, although the projection position of the aforementioned point i moves on the FPD 4, the moving speed of the projection position increases as the distance between the point I before the projection and the reference cutting plane MA increases. Utilizing it, by restructuring the series of subject images obtained while shifting in the body axis direction A at a predetermined pitch, a tomographic image D at a cutting plane parallel to the reference cutting plane MA can be obtained. Such reconstruction of the series of subject images is performed by the image reconstruction block/section 13.

The collimator 3a will be explained concretely. The collimator 3a is a member that restricts the irradiation range of the X-ray passed through the below-mentioned holder 25.

Figure 3:
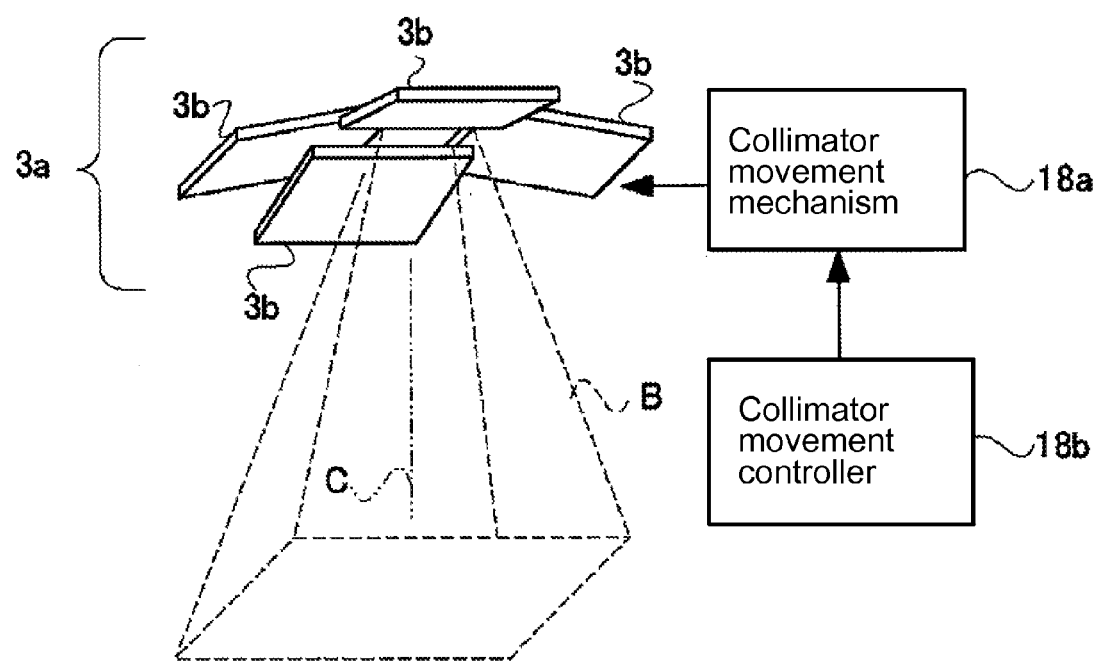
FIG. 3 is a functional block diagram explaining a collimator according to Embodiment 1.

FIG. 3 is a view explaining the structure of the collimator 3a. The collimator 3a is, as shown in FIG. 3, provided with a pair of leaves 3b that move in a mirror symmetric manner with the reference to the central axis C and another pair of leaves 3b that move in a mirror symmetric manner with reference to the central axis C. In this collimator 3a, by moving the leaves 3b, the corn-shaped X-ray beam B can be irradiated on the entire surface of the detection plane of the FPD 4, and further, for example, a fan-shaped X-ray beam B can be irradiated only on the central portion of the FPD 4. The central axis C is also an axis showing the center of the X-ray beam B. One pair of the leaves 3b is configured to adjust the spread of the four-pyramid shaped X-ray beam in the body axis direction A, and the other pair of leaves 3b is configured to adjust the spread of the X-ray beam in the body width direction S.

The change of opening degree of the collimator 3a is performed by the collimator movement mechanism 18a. The collimator movement controller 18b controls the collimator movement mechanism 18a and is controlled by the main controller 30. Further, it can be configured such that the collimator 3a is not moved in a mirror symmetric manner but the pair of leaves 3b are moved independently. The positional relationship between the collimator 3a and the X-ray tube 3 is not changed in accordance with the movement/inclination of the X-ray tube 3, and the collimator 3a follows the movement/inclination of the X-ray tube 3.

Figure 4:
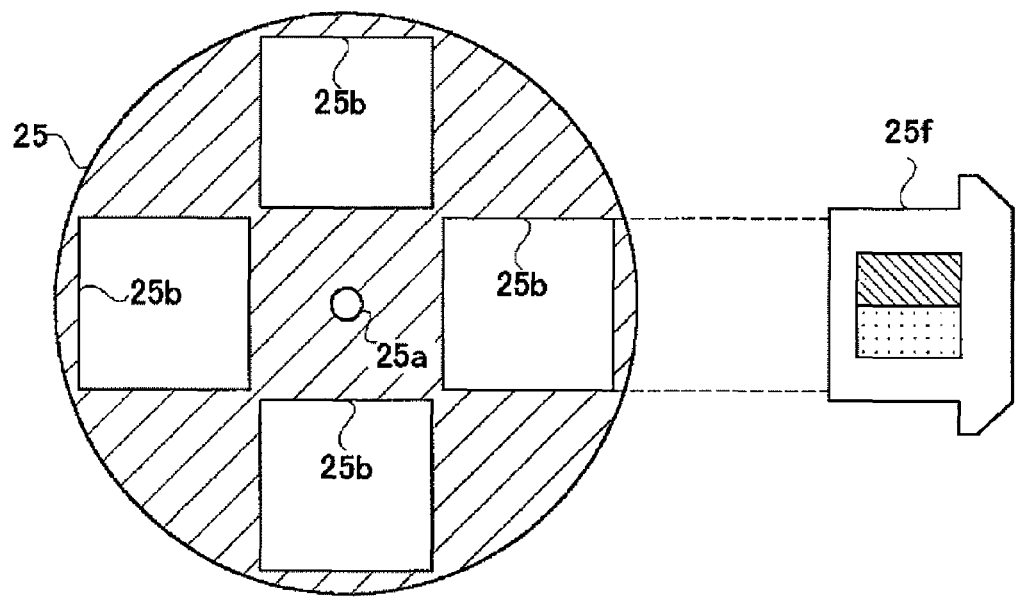
FIG. 4 is a plan view explaining the structure of the holder according to Embodiment 1.

FIG. 4 shows the structure of the holder 25 according to the structure of Embodiment 1. The holder 25 holds the filter 25f through which an X-ray passes. This holder 25 is a disk-shaped member extending on the plane perpendicular to the irradiation direction of the X-ray beam B. The holder 25 is arranged at the position in between the X-ray tube 3 and the collimator 3a. Therefore, the X-ray beam irradiated from the X-ray tube 3 passes through the holder 25 and then reaches the collimator 3a. The holder 25 is held at the X-ray tube 3 and therefore the positional relationship between the holder 25 and the X-ray tube 3 is not changed by the movement/inclination of the X-ray tube 3, and follows the movement/inclination of the X-ray tube 3.

The holder 25 can be rotated with respect to the X-ray tube 3. For example, at the center of the holder 25, a central axis 25a extending in the irradiation direction of the X-ray beam is provided, so that the holder 25 can be rotated about this central axis 25a. The rotational driving of the holder 25 is executed by the holder rotation mechanism 21, also referred to herein as a holder rotator or holder rotator device, or more generally as a holder mover or holder moving device or mechanism. The holder rotation mechanism 21 may include, for example, a rotating motor or other electromechanical movement device. The holder rotation controller 22 is provided for the purpose of controlling the holder rotation mechanism 21. The holder rotation controller 22 may include, for example, hardware and/or software configured to control the holder rotation mechanism 21. For example, the holder rotation controller 22 may include one or more circuits, such as integrated circuits, and may further include program code, configured to control the movement of the holder rotation mechanism 21 to implement the various control methods described herein. These movements may be controlled, for example, according to instructions received from the main controller 30 of FIG. 1, or from another system controller. The holder rotation controller 22 corresponds to the holder rotation control means of the present disclosure. The holder rotation mechanism 21 corresponds to the holder rotation means of the present disclosure.

In the holder 25, a plurality of rectangular holes 25b, also described as openings, are provided. This hole 25b penetrates the holder 25 in the irradiation direction of the X-ray beam. Therefore, the hole 25b penetrates the holder 25 in the central axis C direction. The holes 25b are arranged so as to surround the central axis 25a of the holder 25. In FIG. 4, four holes 25b are provided, but the number of the holes 25b can be arbitrarily changed. These holes are through-holes formed in the holder 25 through which the X-ray beam passes. Though depicted as rectangular, these holes can have other shapes.

The following explanation is directed to how the holder 25 holds the filter 25f. The filter 25f is fixed to the holder 25 so as to close the hole 25b. FIG. 4 shows the state in which the filter 25f is removed from the holder 25. The filter 25f is a plate-shaped member which is thin in the irradiation direction of the X-ray beam.

The filter 25f to be attached to the holder 25 will be explained. This filter 25f is for taking a subtraction image. For example, the filter 25f is a dual purpose filter for a high dose image taking operation and for a low dose image taking operation. The filter 25f is, as shown in FIG. 4, a plate-shaped member larger than the hole 25b of the holder 25. As such, the hole 25b may accommodate the filter 25f.

Figure 5:
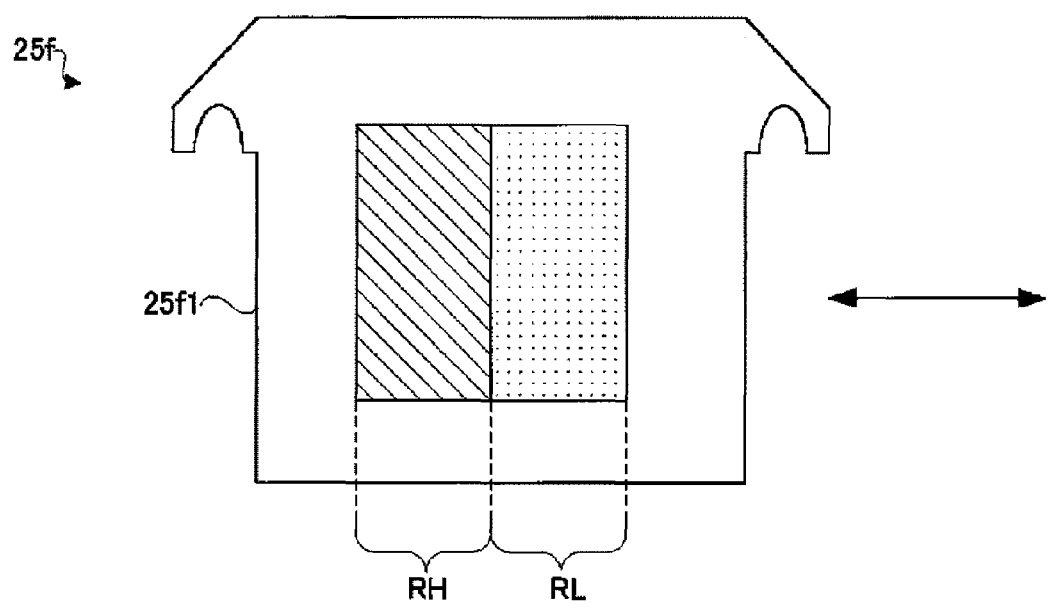
FIG. 5 is a plan view explaining the structure of the filter according to Embodiment 1.

FIG. 5 is a view for explaining a concrete structure of the filter 25f. The filter 25f is structured such that a copper plate shown by hatched lines and a gadolinium plate shown by shading are adhered on the aluminum plate 25f1. The copper plate is arranged at the position where an X-ray passes through at the time of executing a high dose image taking operation, and the gadolinium plate is arranged at the position where an X-ray passes through at the time of executing a low dose image taking operation. The portion of the filter 25f to which the copper plate is attached is a high voltage region RH through which an X-ray irradiated in a state in which the X-ray tube 3 in a high voltage state passes. The portion of the filter 25f to which the gadolinium plate is attached is a low voltage region RL through which an X-ray irradiated in a state in which the X-ray tube 3 is in a low voltage state passes.

The arrangement of the high voltage region RH and the low voltage region RL in the filter 25f will be explained. In one embodiment, the high voltage region RH and the low voltage region RL are provided adjacently with no gap therebetween, and arranged in the direction shown by the arrow in FIG. 5. This arrow direction is a direction along which the filter 25f moves in accordance with the rotation of the holder 25 in a state in which the filter 25f is fixed to the holder 25. Therefore, when the holder 25 is slightly rotated in a state in which the high voltage region RH is set to the X-ray tube 3, it turns into a state in which the low voltage region RL is set to the X-ray tube 3.

Figure 6:
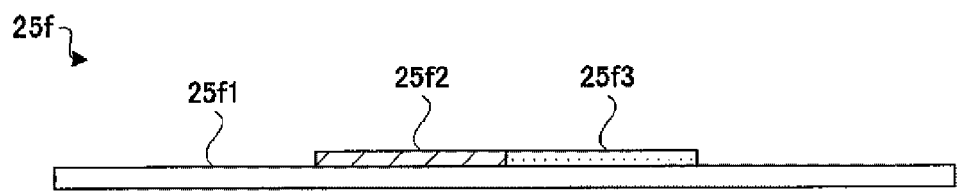
FIG. 6 is a cross-sectional view explaining the structure of the filter according to Embodiment 1.

FIG. 6 shows the cross-section of the filter 25f. The filter 25f is, as shown in FIG. 6, constituted such that the copper plate 25f2 and the gadolinium plate 25f3 are adhered to the aluminum plate 25f1. Therefore, when an X-ray beam passes through the copper plate 25f2, the X-ray also passes through the aluminum plate 25f1. This is also the same in the gadolinium plate 25f3.

Figure 7:
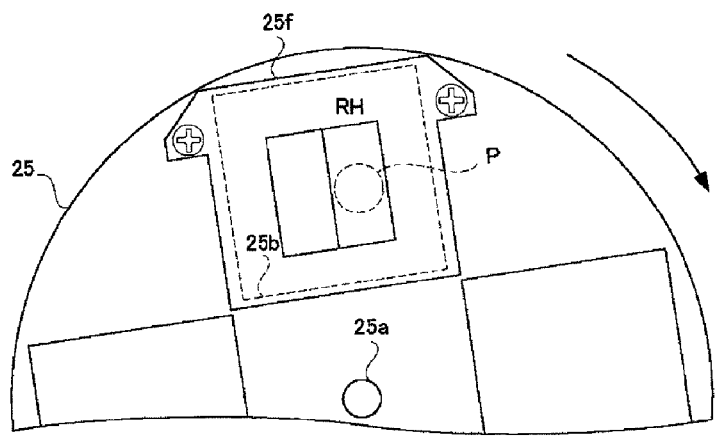
FIG. 7 is a plan view explaining the rotation of the holder according to Embodiment 1.

FIG. 7 shows a state in which the high voltage region RH of the filter 25f is set to the X-ray tube 3. The region P shows a passage through which the X-ray irradiated from the X-ray tube 3 passes. In the structure of FIG. 7, the X-ray irradiated from the X-ray tube 3 passes through the aluminum plate 25f1 and the copper plate 25f2 of the filter 25f and advances toward the collimator 3a. At this time, since the hole 25b is formed in the holder 25, the X-ray does not penetrate the member constituting the holder 25.

FIG. 7 shows the state in which the filter 25f is screwed to the holder 25. The screw is secured to the holder 25 in a state in which the screw is fitted in the screw engaging concave portion (see FIG. 5) formed in the filter 25f.

Figure 8:
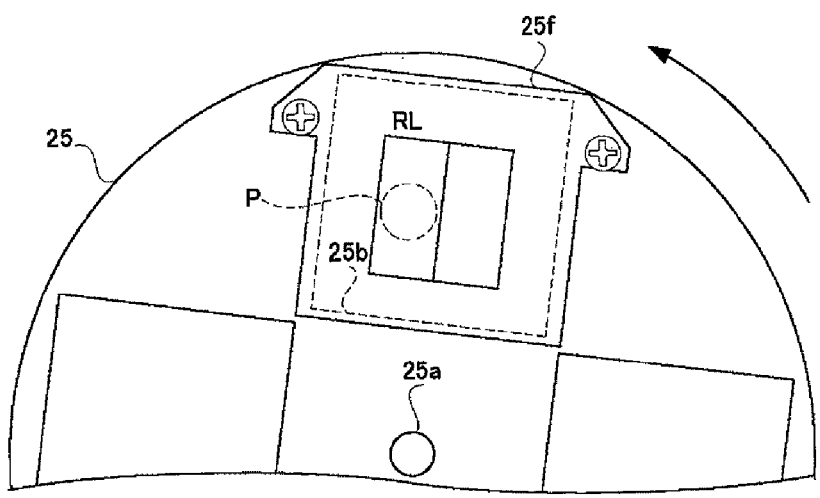
FIG. 8 is a plan view explaining the rotation of the holder according to Embodiment 1.

FIG. 8 shows a state in which the low voltage region RL of the filter 25f is set to the X-ray tube 3. The region P shows a passage through which an X-ray irradiated from the X-ray tube 3 passes. In the structure shown in FIG. 8, the X-ray irradiated from the X-ray tube 3 passes through the aluminum plate 25f1 and the gadolinium plate 25f3 of the filter 25f and advances toward the collimator 3a. At this time, since the hole 25b is formed in the holder 25, the X-ray does not penetrate the member constituting the holder 25.

Changing the region to be set to the X-ray tube 3 will be explained. In order to change from the state in which the high voltage region RH is set to the X-ray tube 3 to the state in which the low voltage region RL is set to the X-ray tube, the holder 25 which is in the state shown in FIG. 7 is rotated in a direction from the low voltage region RL to the high voltage region RH so that the holder 25 becomes the state shown in FIG. 8. On the other hand, in order to change from the state in which the low voltage region RL is set to the X-ray tube 3 to the state in which the high voltage region RH is set to the X-ray tube, the holder which is in the state shown in FIG. 8 is rotated in a direction from the high voltage region RH to the low voltage region RL so that the holder 25 becomes the state shown in FIG. 7. The positional relationship between the central axis 25*a* and the region P will not change in accordance with the rotation of the holder 25.

As mentioned above, at the time of taking a subtraction image, the holder rotation mechanism 21 rotates the holder 25 to thereby move the high voltage region of the filter 25*f* to the position where an X-ray passes through when the X-ray tube 3 is in a high voltage state and move the low voltage region of the filter 25*f* where an X-ray passes through when the X-ray tube 3 is in a low voltage state. Concretely, when moving the low voltage region RL of the filter 25*f* to the position where an X-ray passes through after moving the high voltage region RH of the filter 25*f* to the position where an X-ray passes through, the holder rotation mechanism 21 inverts the rotational direction of the holder 25. Further, when moving the high voltage region RH of the filter 25*f* to the position where an X-ray passes through after moving the low voltage region RL of the filter 25*f* to the position where an X-ray passes through, the holder rotation mechanism 21 again inverts the rotational direction of the holder 25. Thus, the holder rotation mechanism 21 has a role of changing the regions.

The holder rotation mechanism 21 has another role. The holder rotation mechanism 21 has a function of switching whether or not the X-ray irradiated from the X-ray tube 3 is allowed to pass through the filter 25*f*. The X-ray equipment 1 is not a dedicated equipment for taking a subtraction image. There is a possibility that this equipment performs an image taking operation other than a subtraction image taking operation. When not taking a subtraction image, the holder rotation mechanism 21 rotates the holder 25 to thereby move the filter 25*f* to the position away from the X-ray tube 3. By setting as mentioned above, it becomes the state in which the X-ray irradiated from the X-ray tube 3 does not pass through the filter 25*f*. At this time, the hole 25*b* other than the hole 25*b* to which the filter 25*f* is inserted will be rotated to the position adjacent to the region P (see FIG. 7). The X-ray irradiated from the X-ray tube 3 passes through this hole 25*b*, no X-ray will penetrate the member constituting the holder 25.

The reason that the X-ray equipment 1 of the present disclosure is provided with the filter 25*f* will be explained below. The filter 25*f* is provided for the purpose of obtaining a subtraction image using two images different in output of the X-ray tube 3. The subtraction image can be generated by subtracting the image obtained by controlling the X-ray tube at a low voltage from the image obtained by controlling the X-ray tube 3 at a high voltage. Comparing two images which are original images for a subtraction image, a soft tissue of a subject M and a bony part of the subject M are different in image depth.

If two images in which the depth of the soft tissue with respect to the bony part is equal with each other are subjected to subtraction processing, the subject images to be seen in an image are simply cancelled out and therefore deleted. However, when two images in which the depth of the soft tissue of the subject M with respect to the depth of the bony part of the subject M are different are subjected to subtraction processing, for example, in a portion of the image in which the soft tissue is seen, there is a phenomenon that cancelling out of the images seldom occurs, and in a portion of the image in which the bony part is seen, there is a phenomenon that cancelling out of the images strongly occurs. In the case of this example, by subjecting the two images to subtraction processing, a subtraction image in which the soft tissue of the subject M is emphasized than the bony part can be obtained. By changing the coefficient for the subtraction processing, the bony part of the subject M can also be emphasized.

In order to obtain a subtraction image high in visibility, it is useful to assuredly differentiate the image density/depth of the soft tissue of the subject M with respect to the image density/depth of the bony part of the subject M between two images to be obtained. Such difference of the image density/depth derives from the difference of characteristics of the X-rays irradiated at the time of taking two images. If two images are taken by irradiating X-rays having the same radiation quality, the image density/depth of the soft tissue with respect to the image density/depth of the bony part becomes similar between two images. Even if the difference of these two images is obtained, subject images seen in the image are merely cancelled out, and the soft tissue of the subject M will not be emphasized.

Figure 9:
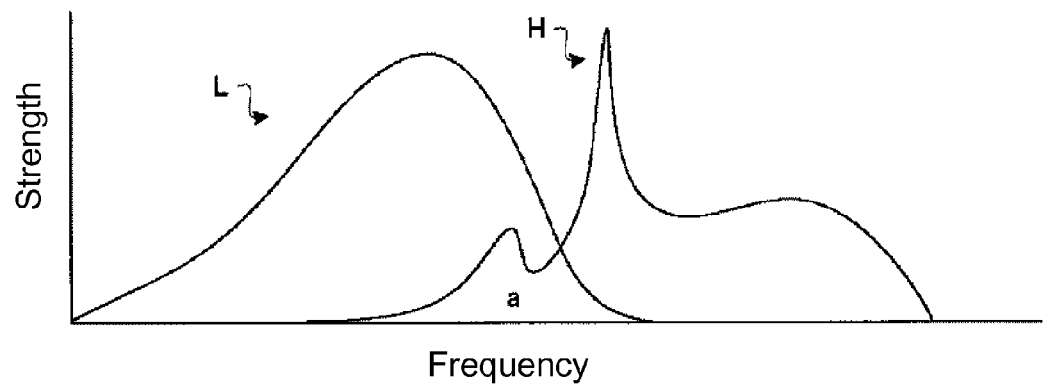
FIG. 9 is a schematic view explaining the function of the filter according to Embodiment 1.

FIG. 9 shows spectrums of X-rays when a subtraction image is obtained without using the filter 25*f*. In this figure, the spectrum of the X-ray irradiated when the X-ray tube 3 was in a high voltage state is denoted by H, and the spectrum of the X-ray irradiated when the X-ray tube 3 was in a low voltage state is denoted by L. From FIG. 9, it is understood that, although these spectrums are different in frequency distribution, there exists a common portion "a" where these spectrums overlap partially. This common portion "a" denotes that X-rays having the same radiation quality are contained in two X-ray irradiations. In order to assuredly differentiate the characteristic of X-rays when the X-ray tube 3 is in a high voltage state and in a low voltage state, it is useful, and may be preferable, to eliminate the common portion "a" as much as possible.

Therefore, when obtaining a subtraction image, the filter 25*f* is used. As such, when the X-ray tube 3 is in a high voltage state, the X-ray passes through the high voltage region RH of the filter 25*f*. The high voltage region RH is configured to cut the low frequency component of the X-ray under the high voltage condition. Further, when the X-ray tube 3 is in a low voltage state, the X-ray passes through the low voltage region RL of the filter 25*f*. The low voltage region RL is configured to cut the high frequency component of the X-ray under the low voltage condition.

Figure 10:
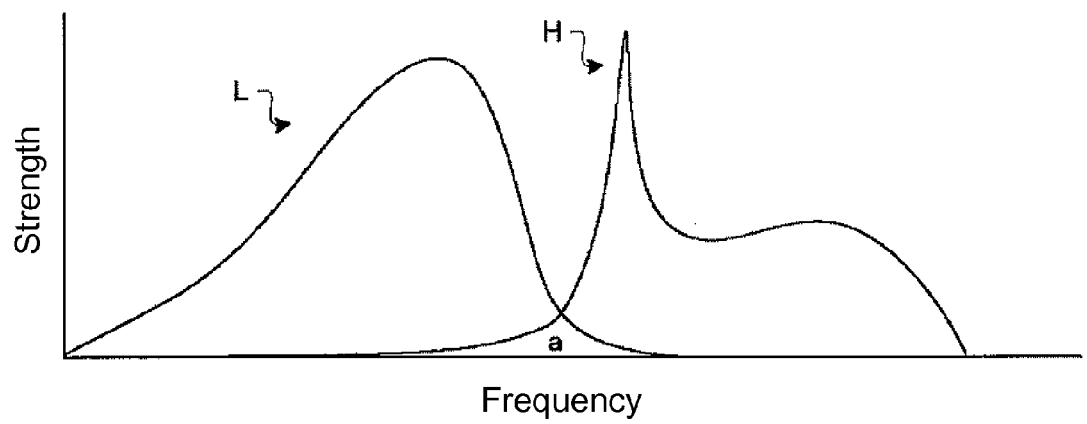
FIG. 10 is a schematic view explaining the function of the filter according to Embodiment 1.

Due to the function of the filter 25*f*, the spectrums of the X-rays irradiated toward the subject M have been changed as shown in FIG. 10. As will be understood from FIG. 10, the common portion "a" of the spectrums H and L is decreased as compared to the state shown in FIG. 9 by the function of the filter 25*f*. As mentioned above, the filter 25*f* is provided for the purpose of assuredly differentiating the characteristics of the X-rays irradiated at the time of taking two images.

<Operation of X-Ray Tomographic Apparatus>

Figure 11:
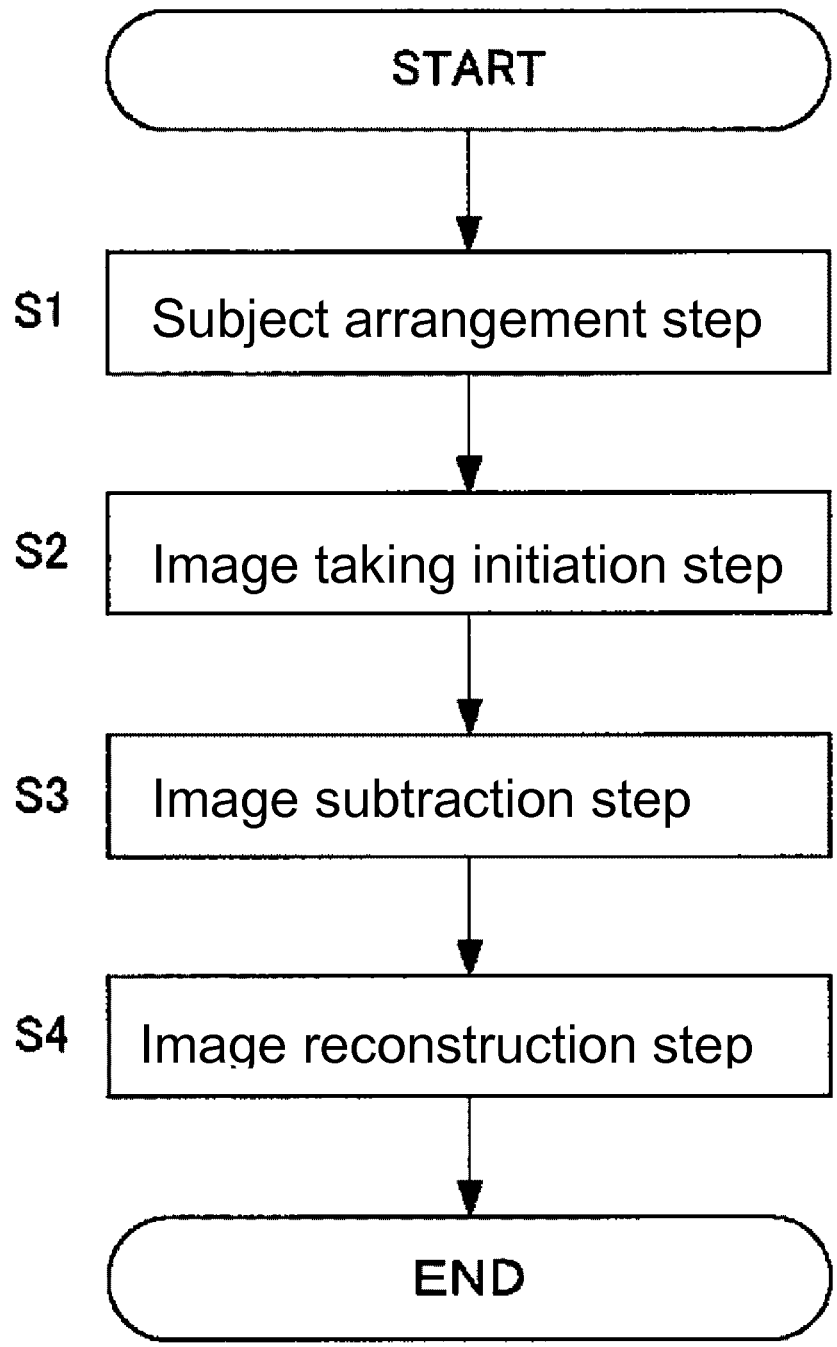
FIG. 11 is a flow chart explaining the operation of the radiographic apparatus according to Embodiment 1.

Next, the operation of the X-ray equipment 1 according to Embodiment 1 will be explained with reference to FIG. 11. In order to obtain a subtraction image of a tomogram using the X-ray equipment 1 according to Embodiment 1, a subject M is initially arranged on the top board 2 (Subject arrangement step S1), and an image taking operation is initiated (Image taking initiation step S2). Subsequently, a subtraction image is generated from continuously taken transparent images P1 taken under a high voltage condition and transparent images P2 taken under a low voltage condition (Image subtraction step S3). Lastly, the subtraction images are reconstructed to thereby obtain a tomographic image D (Image reconstruction step S4). Hereinafter, each step will be explained.

In Embodiment 1, it is structured such that an image taking operation under a high voltage condition and an image taking operation under a low voltage condition are performed alternately.

<Subject Arrangement Step S1, Image Taking Initiation Step S2>

When an operator gives an instruction of initiating an image taking operation to the X-ray equipment 1 through the console 26 after arranging the subject M on the top board 2, the X-ray tube controller 6 reads out setting values regarding the control of the X-ray tube 3, such as, e.g., a tube voltage, a tube current, or a pulse width, stored in the storage 23. The X-ray tube controller 6 controls the X-ray tube 3 in accordance with the settings to make the X-ray tube 3 generate an X-ray. The X-ray passed through the subject M is detected by the FPD 4, and the detection signal is transmitted to the image generation block/section 11. The image generation block/section 11 generates a transparent image in which a transparent image of the subject M is seen based on the detection signal.

At this time, the setting values read out to the X-ray tube controller 6 include both a setting value for a high voltage image taking operation and a setting value for a low voltage image taking operation. A symbol P1 will be allotted to the X-ray transparent image taken under a high voltage condition, and a symbol P2 will be allotted to the X-ray transparent image taken under a low voltage condition.

The X-ray tube controller 6 transmits the information that an image taking operation is performed under a high voltage condition to the holder rotation controller 22 before performing the operation. Then, the holder rotation controller 22 rotates the holder 25 via the holder rotation mechanism 21 so that the high voltage region RH of the filter 25f is set to the X-ray tube 3. In the same manner, the X-ray tube controller 6 transmits the information that an image taking operation is performed under a low voltage condition to the holder rotation controller 22 before performing the operation. Then, the holder rotation controller 22 rotates the holder 25 via the holder rotation mechanism 21 so that the low voltage region RL of the filter 25f is set to the X-ray tube 3.

Figure 12:
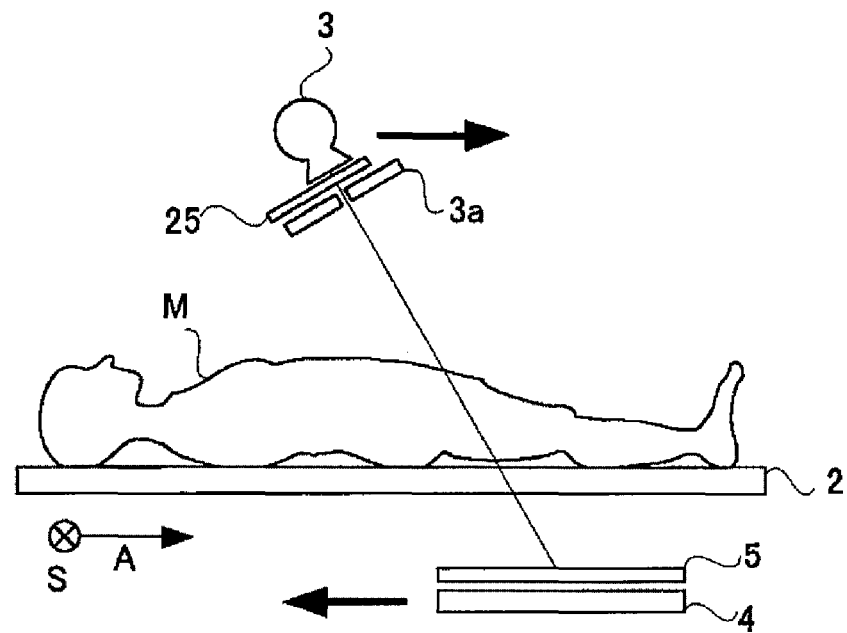
FIG. 12 is a schematic view explaining the operation of the radiographic apparatus according to Embodiment 1.
Figure 13:
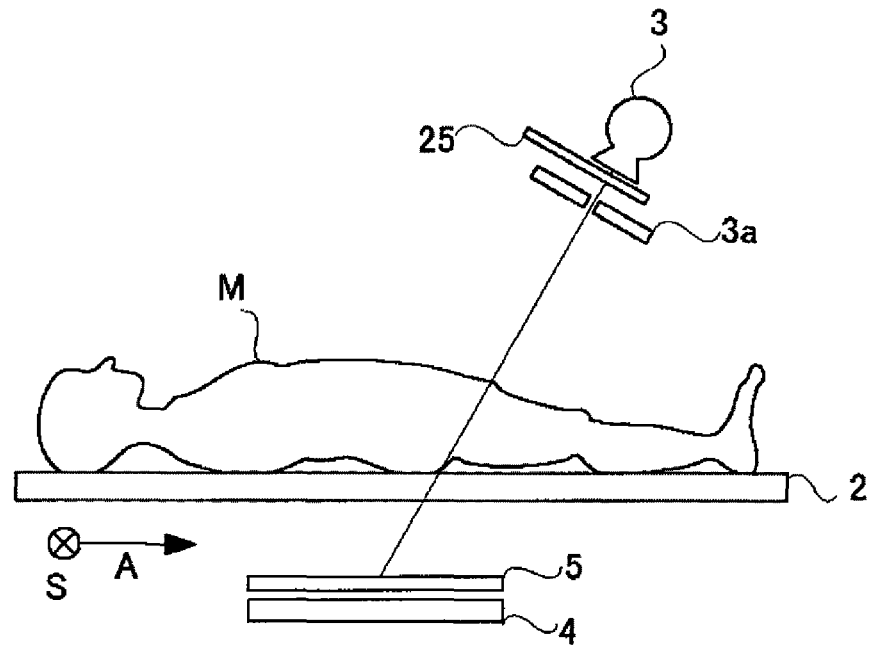
FIG. 13 is a schematic view explaining the operation of the radiographic apparatus according to Embodiment 1.

FIG. 12 shows the state immediately before initiating an image taking operation. When the image taking operation is initiated, the X-ray tube 3 in a state shown by FIG. 12 continuously irradiates X-rays while moving in one direction advancing from the head portion of the subject M toward the toe thereof with respect to the subject M. At this time, the X-ray tube 3 alternately performs an X-ray irradiation at a high voltage and an X-ray irradiation at a low voltage. Further, the FPD 4 detects the X-rays while moving in an opposite direction advancing from the toe of the subject M toward the head portion thereof with respect to the subject M. The filter used for taking a series of transparent images P1 is the same filter for taking subtraction images. Between the image taking operations, the holder 25 rotates in a swinging manner (for example, it may swing back and forth over a series of image taking operations). With this, the high voltage region RH of the filter 25f is used for a high voltage image taking operation, and the low voltage region RL of the filter 25f is used for a low voltage image taking operation. In one embodiment, the transparent images P1 and the transparent images P2 are obtained by 72 images, respectively. FIG. 13 shows the state immediately after completion of the image taking operation.

<Image Subtraction Step S3>

The transparent images P1 and the transparent images P2 are transmitted to the image subtraction block/section 12. The image subtraction block/section 12 obtains the difference between the transparent image P1 and the transparent image P2 to generate a subtraction image.

The relation of the transparent image P1 and the transparent image P2 will be explained. The transparent image P1 and the transparent image P2 are transparent images of the subject M taken under almost the same conditions except that the voltage condition of the X-ray tube 3 differs. More specifically, before and after taking each of the 74 transparent images P1, a transparent image P2 is taken. In other words, the transparent image P2 is taken under almost the same positional relationship as the positional relationship of the subject, the X-ray tube 3, and the FPD 4 at the time of taking a transparent image P1.

The image subtraction block/section 12 obtains the difference between a transparent image P1 and the corresponding transparent image P2 to thereby obtain a subtraction image. Since the transparent images P1 and the transparent images P2 are taken by 74 images, respectively, subtraction images will also be obtained by 74 images. In each of subtraction images, an image in which a soft tissue or a bony part of the subject M is emphasized is seen. By changing the coefficient used for the difference calculation, the image subtraction section 12 can adjust the image emphasis state in the subtraction image.

<Image Reconstruction Step S4>

The 74 subtraction images will be transmitted to the image reconstruction block/section 13. The image reconstruction block/section 13 reconstructs the series of subtraction images in which subject images different in the projection direction of the image taking operation are seen to generate a tomographic image D. As explained above, the image reconstruction block/section 13 generates a tomographic image obtained by cutting the subject M with a virtual plane as a composite image. The tomographic image D is displayed on the display 27, and the operation of the X-ray equipment 1 terminates.

As explained above, according to the present disclosure, in the X-ray equipment 1 configured such that the X-ray tube 3 moves with respect to the subject M, it is structured to generate a subtraction image by obtaining the difference between an image taken at the high voltage state and an image taken at the low voltage state. According to the structure of the present disclosure, by rotating the holder 25, it becomes possible to switch whether or not the X-ray irradiated from the X-ray tube 3 is caused to pass through the filter 25f for taking a subtraction image. In other words, in cases where it is desired to perform an image taking operation in a state in which an X-ray does not pass through the filter 25f for taking a subtraction image after performing an image taking operation in a state in which an X-ray passes through the filter 25f for taking a subtraction image, the image taking operation can be continuously performed immediately by rotating the holder. This is because, according to the equipment of the present disclosure, it becomes possible to deal with changing of image taking methods by merely rotating the holder 25 between intervals of image taking operations. Although the apparatus according to the present disclosure is an apparatus capable of performing a subtraction image taking operation, it is possible to immediately perform an image taking operation other than a subtraction image taking operation. Therefore, according to the present disclosure, it becomes possible to provide an X-ray equipment capable of flexibly perform image taking operations.

Further, when moving one of regions of the filter 25*f* to the position through which an X-ray passes and then moving the other of regions of the filter 25*f* to the position through which an X-ray passes, by inverting the rotation direction of the holder 25, it becomes possible to take a subtraction image by merely slightly moving the filter 25*f*.

In the case of providing a collimator that limits the irradiation range of an X-ray passed through the holder 25, the holder 25 inevitably is arranged at the position in between the X-ray tube 3 and the collimator. By structuring as mentioned above, it becomes possible to arrange the filter 25*f* provided at the holder 25 and the X-ray tube 3 in an adjacent manner. Thus, the filter 25*f* can be reduced in size. This is because the width of the X-ray irradiated from the X-ray tube 3 is the smallest immediately after the irradiation.

Embodiment 2

Figure 14:
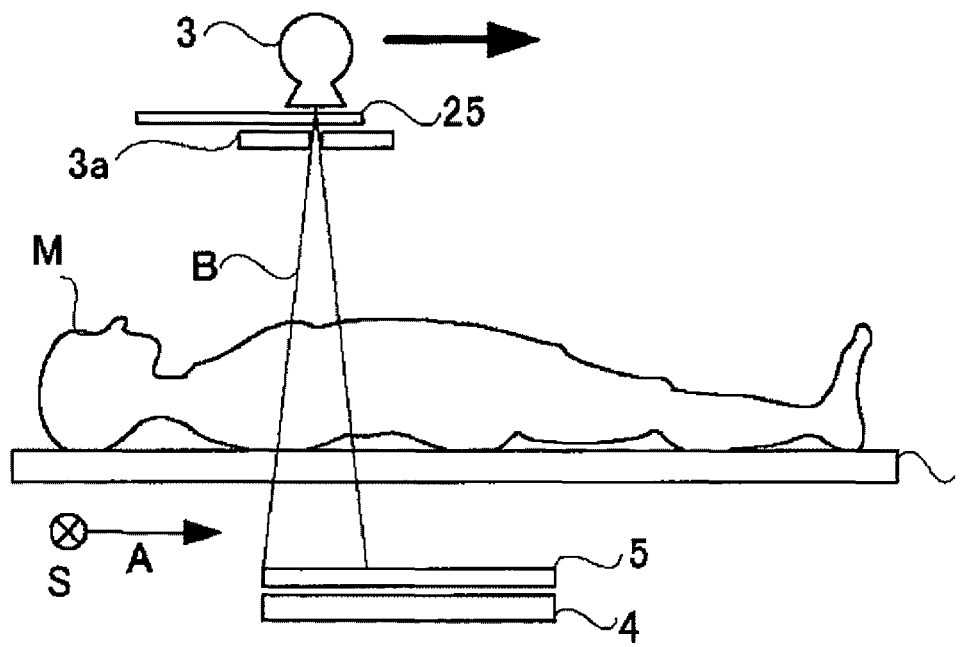
FIG. 14 is a schematic view explaining the operation of the radiographic apparatus according to Embodiment 2.
Figure 15:
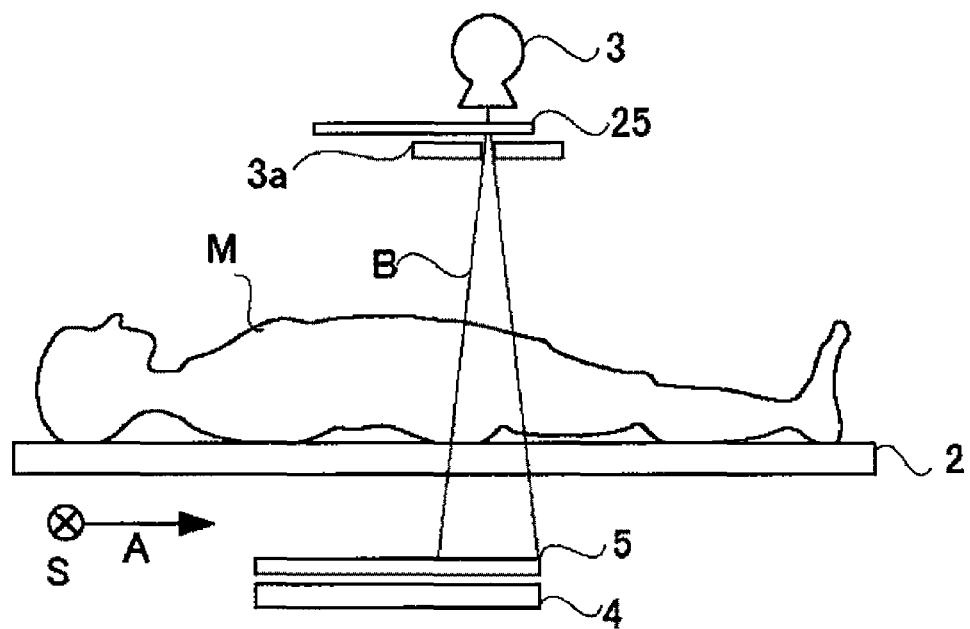
FIG. 15 is a schematic view explaining the operation of the radiographic apparatus according to Embodiment 2.

Subsequently, an X-ray equipment according to Embodiment 2 will be explained with reference to FIGS. 14 and 15. In Embodiment 2, an image taking operation is performed in such a manner that the X-ray tube 3 is moved but the FPD 4 is not moved. The structure of the X-ray equipment according to Embodiment 2 is the same as that of Embodiment 1 having the function block shown in FIG. 1. With respect to FIG. 1, the structure of Embodiment 2 differs from that of Embodiment 1 in that the FPD 4 does not move, the X-ray tube 3 is not inclined, and a tomographic image is not generated. In Embodiment 2, it is not always required to equip the synchronous movement mechanism 7, the FPD movement mechanism 7*b*, the synchronous movement controller 8, the FPD movement controller 8*b*, the X-ray tube tilt mechanism 9, the X-ray tube tilt controller 10, and the image reconstruction block/section 13.

Embodiment 2 employs the structure that an image taking operation under a high voltage condition and an image taking operation under a low voltage condition are performed alternately.

In the X-ray equipment according to Embodiment 2, the X-ray irradiated from the X-ray tube 3 is limited by the collimator 3*a*. The collimator 3*a* limits the spreading of the X-ray in the body axis direction, and therefore a fun-shaped X-ray beam elongated in the body width direction S reaches the FPD 4. For example, in the X-ray equipment according to Embodiment 2, an X-ray transparent image elongated in the body width direction S of the subject M can be obtained by a single X-ray irradiation. This elongated image is taken by a plurality of times, and the images are arranged in the body axis direction to thereby form a single composite image. It becomes possible to reduce the amount of scattered rays seen in an image by dividing the X-ray image taking operation into plural operations and taking plural images of the subject M little by little. Therefore, it becomes possible to determine the quantity of bone mineral with high quantitativity. Such an image taking operation by the X-ray limited in spreading is called a slot image taking operation.

The image reconstruction block/section 13 of Embodiment 2 will not perform the operation for creating a tomographic image D as explained in Embodiment 1. The image reconstruction block/section 13 joins subtraction images taken while changing the position of the X-ray tube 3 with respect to the subject M to thereby generate a single composite image. For example, in one embodiment, the image reconstruction block/section 13 arranges and joins subtraction images elongated in the body width direction S of the subject M in the body axis direction A of the subject M to thereby generate a composite image.

<Operation of X-Ray Equipment>

The operation of the X-ray equipment according to Embodiment 2 is similar to the operation of the equipment according to Embodiment 1 explained with reference to FIG. 11. FIG. 14 shows a state immediately before initiation of the image taking operation in the image taking initiation step S2. As shown in FIG. 14, the X-ray tube 3 is positioned at one of both ends of the FPD 4 which is a head side of the subject M, and advances toward the toe side of the subject M in one direction while intermittently irradiating X-ray beams B. At this time, the FPD 4 does not move. When the X-ray tube 3 reaches the toe side of the subject M, the image taking operation terminates. FIG. 15 shows a state immediately after termination of the image taking operation. The control of the X-ray tube 3 and the holder 25 during this image taking operation is the same as in Embodiment 1, and therefore the explanation will be omitted.

As explained above, Embodiment 2 is directed to a radiographic apparatus for determining the quantity of bone mineral. When performing a bone mineral quantity determination, a slot image taking operation is performed in a manner such that the X-ray tube 3 is moved with respect to the subject M but the FPD 4 is not moved with respect to the subject M. The present disclosure can be applied to such a structure.

Embodiment 3

Figure 16:
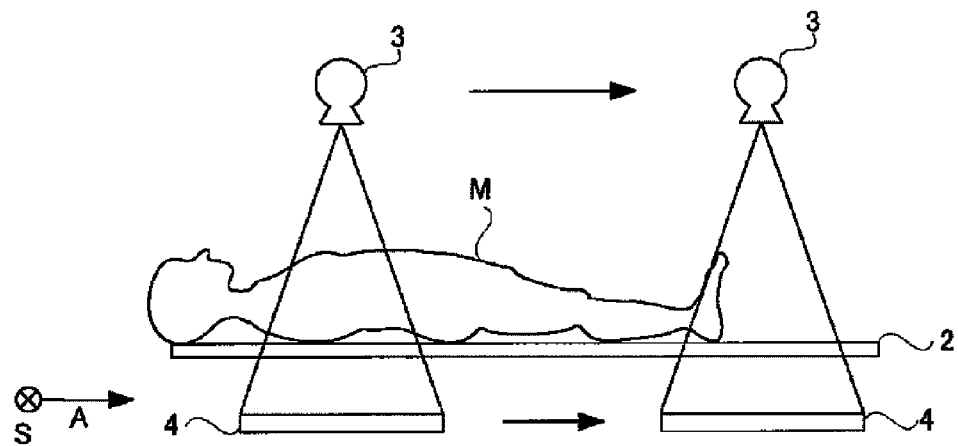
FIG. 16 is a schematic view explaining the operation of the radiographic apparatus according to Embodiment 3.

Next, an X-ray tomographic apparatus according to Embodiment 3 will be explained with reference to FIGS. 16 to 21. In Embodiment 3, as shown in FIG. 16, it is structured such that tomographic images can be taken while moving the X-ray tube 3 and the FPD 4 in the body axis direction A of the subject M in a state in which the positional relationship of the X-ray tube 3 and the FPD 4 is kept. At this time, as the image taking method, not a slot image taking method like in Embodiment 2 but an image taking method in which an X-ray is irradiated to the whole area of the FPD 4 is employed.

In Embodiment 3, it is structured such that an image taking operation under a high voltage condition and an image taking operation under a low voltage condition are performed alternately.

The structure of the X-ray equipment according to Embodiment 3 is the same as the functional block diagram shown in FIG. 1. Regarding FIG. 1, the structure of Embodiment 3 differs from that of Embodiment 1 in that the FPD 4 moves while following the X-ray tube 3 (see FIG. 16) and the X-ray tube 3 does not tilt. Therefore, in Embodiment 3, the X-ray tilt mechanism 9 and the X-ray tube tilt controller 10 shown in FIG. 1 are not always required.

The principle of taking a tomographic image according to Embodiment 3 will be explained. Initially, as shown in FIG. 16, in a state in which the imaging system 3 and 4 keeps the relative position, X-rays are irradiated intermittently to the subject M while moving with respect to the subject M. For example, in one embodiment, every time a single irradiation terminates, the X-ray tube 3 moves in the body axis direction A of the subject M and again irradiates an X-ray. Thus, a plurality of transparent images are obtained, and the processed image (below-mentioned elongated transparent image) of the transparent image is reconstructed into a tomographic image by a filter back projection method. The completed tomographic image is an image in which a tomogram of the subject M obtained by cutting the subject M with a cutting plane is seen.

Figure 17:
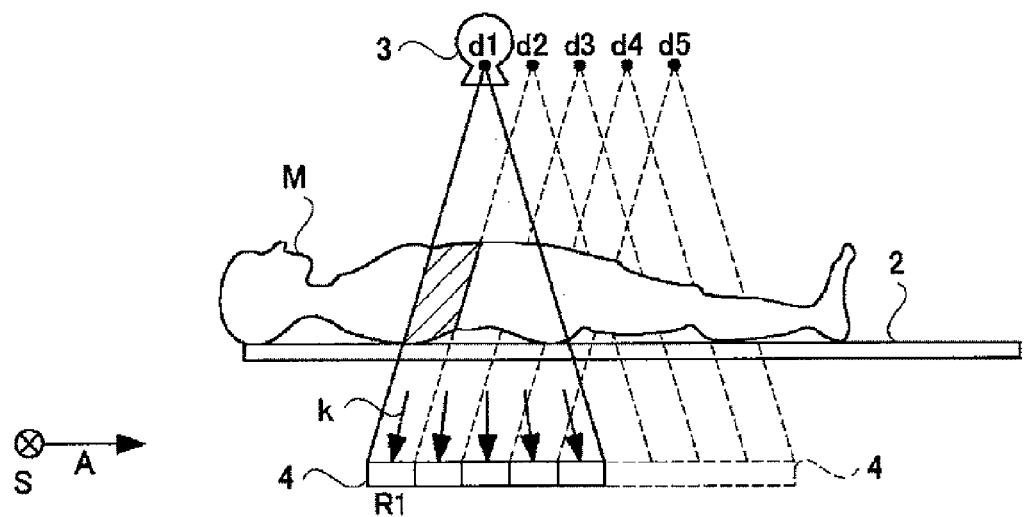
FIG. 17 is a schematic view explaining an image taking principle of the radiographic apparatus according to Embodiment 3.

To create a tomographic image, images of a subject M seen through from different directions are required. The X-ray tomographic apparatus according to Embodiment 3 is configured to divide the obtained transparent image and join them to create an image. This operation will be explained. FIG. 17 shows a position of the FPD 4 when the X-ray irradiation focal point of the X-ray tube 3 is positioned at d1. In this image taking operation, it is supposed that a transparent image is taken every time the X-ray tube 3 and the FPD 4 moves in the body axis direction A of the subject M with respect to the top board 2 by ⅕ of the width of the FPD 4.

The X-ray spreads from the X-ray tube 3 and reaches the FPD 4. When the created transparent image is divided into five in the body axis direction A of the subject M, the incident angles of the X-ray with respect to the FPD 4 differ among the divided sections as shown in the arrow. A certain one direction k among the directions will be focused on. The X-ray irradiated in this direction k passes through the shaded portion of the subject M and reaches the FPD 4. Therefore, in the divided section of the FPD 4 in which the X-ray of the direction k is entered, the shaded portion of the subject M is seen. In the transparent image, the portion of this transparent image corresponding to this divided section will be referred to as a segment R1.

Figure 18:
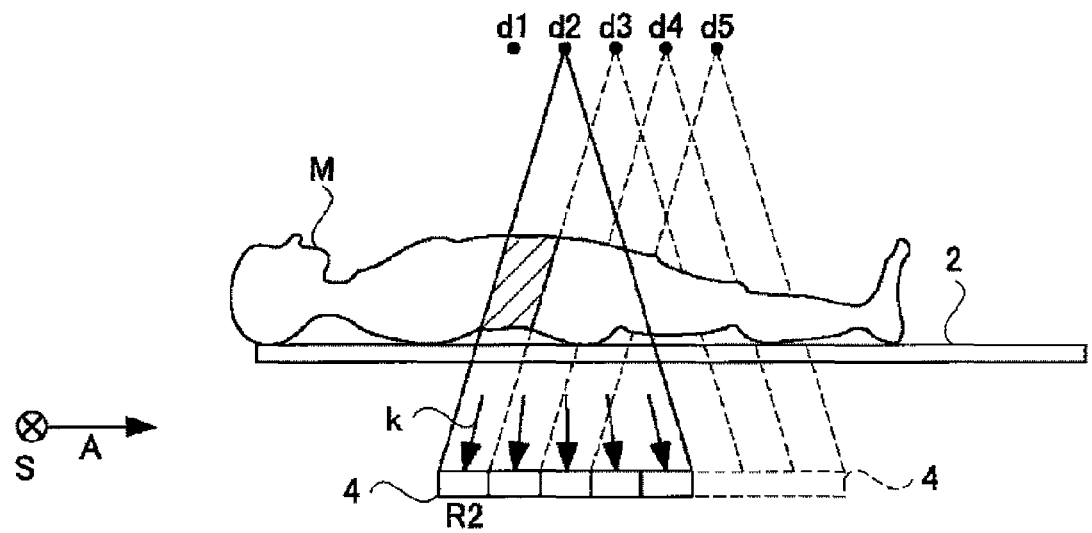
FIG. 18 is a schematic view explaining an image taking principle of the radiographic apparatus according to Embodiment 3.

FIG. 18 shows a position of the FPD 4 when the X-ray irradiation focal point of the X-ray tube 3 is moved from d1 to d2 by ⅕ of the width of the FPD 4. Since the positional relationship between the X-ray tube 3 and the FPD 4 does not change, in the FPD 4 at the time of this image taking operation, there should exist a divided section in which the X-ray advanced in the direction k is entered. In the divided section of the FPD 4 in which the X-ray of the direction k is entered, the shaded portion of the subject M is seen. In the transparent image, the portion corresponding to this divided section will be referred to as a segment R2.

Figure 19:
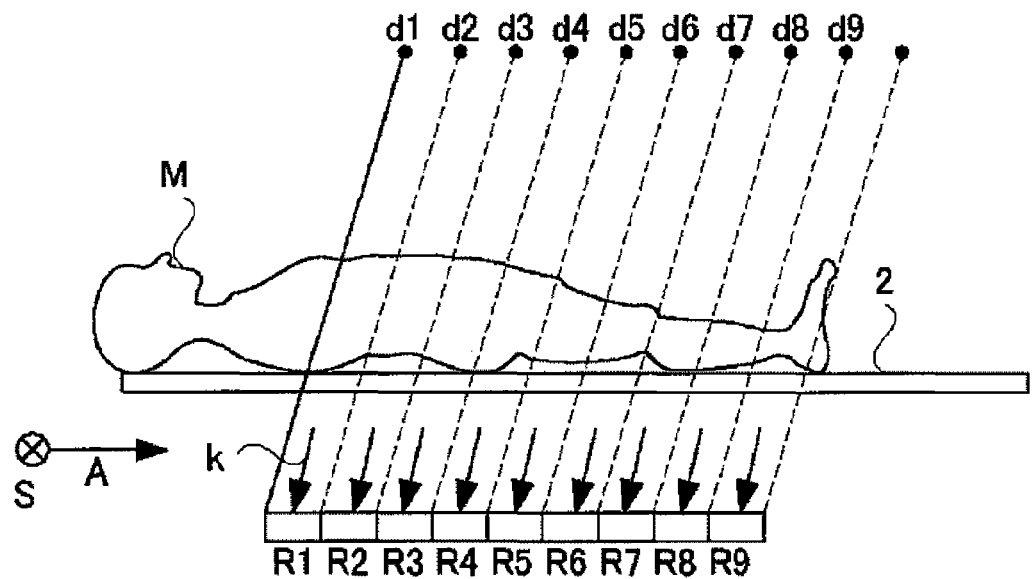
FIG. 19 is a schematic view explaining an image taking principle of the radiographic apparatus according to Embodiment 3.

Comparing the segment R1 and the segment R2, the position of the subject M with respect to the imaging system 3 and 4 differs, and therefore the portions of the subject M in which both segments R1 and R2 are seen differ. In cases where 9 (nine) image taking operations are performed at the focal points d1-d9 while shifting the X-ray tube 3 by ⅕ of the width of the FPD 4, in each of the segments R1-R9 of the transparent image in the divided sections of the FPD 4 in which the X-ray of the direction k is entered, portions of the subject M different in position are seen. Therefore, by joining the segments R1-R9 of the transparent image as shown in FIG. 19 in this order in the body axis direction A of the subject M, an image taken when an X-ray is irradiated to the entire body of the subject M at a certain direction k can be obtained. This image will be referred to as an elongated transparent image. The elongated image corresponds to an intermediate image of the present disclosure.

The X-ray tomographic apparatus according to Embodiment 3 generates elongated transparent images of directions other than the direction k in the image reconstruction block/section 13. Then, the image reconstruction block/section 13 generates a tomographic image obtained by cutting the subject M at a certain cutting position based on a plurality of elongated transparent images different in projection direction of the subject M.

<Operation of X-Ray Tomographic Apparatus>

The operation of the X-ray equipment according to Embodiment 3 is the same as that of the equipment according to Embodiment 1 explained with reference to FIG. 11.

Figure 20:
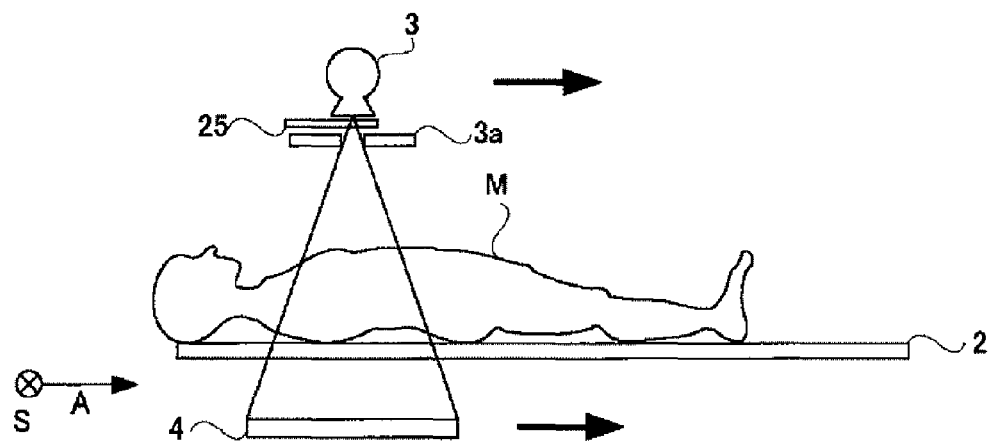
FIG. 20 is a schematic view explaining the operation of the radiographic apparatus according to Embodiment 3.
Figure 21:
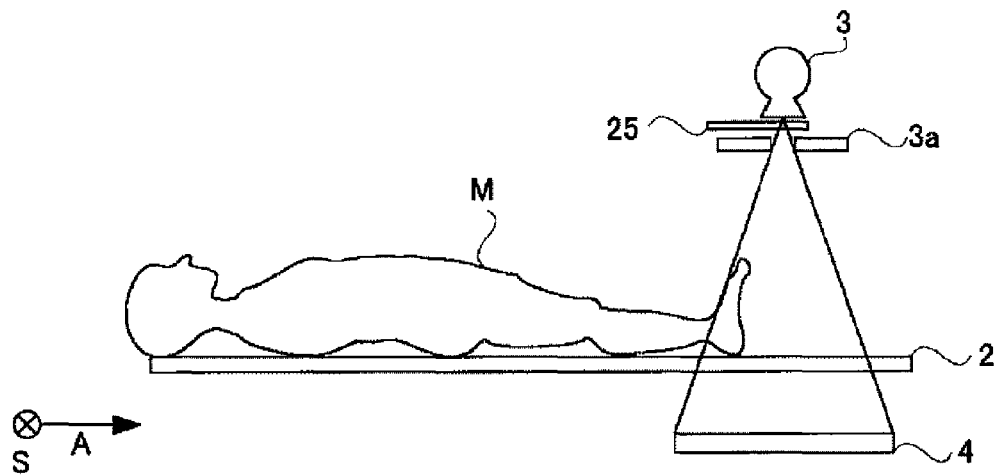
FIG. 21 is a schematic view explaining the operation of the radiographic apparatus according to Embodiment 3.

FIG. 20 shows a state immediately before initiation of the image taking operation in the image taking initiation step S2. As shown in FIG. 20, the X-ray tube 3 and the FPD 4 are positioned at the head side of the subject M, and move in one direction while intermittently taking transparent images in a continuous manner toward the toe side of the subject M. When the X-ray tube 3 and the FPD 4 reach the toe side of the subject M, the image taking operation terminates. The control of the X-ray tube 3 and the holder 25 during this image taking operation is the same as that in Embodiment 1, and therefore the explanation will be omitted. FIG. 21 shows a state immediately after termination of the image taking operation.

The image subtraction block/section 12 obtains a subtraction image by obtaining the difference between each of the transparent images P1 and its corresponding transparent image P2 in the image subtraction step S3. The transparent image P2 corresponding to the transparent image P1 denotes a transparent image P2 taken before and after taking the transparent image P1. At this time, the same number of subtraction images as the transparent images P1 are obtained.

The image reconstruction block/section 13 obtains a plurality of subtraction images in the image reconstruction step S4. The image reconstruction block/section 13 divides each of subtraction images into strip-like images extending in the body width direction s of the subject M. Thereafter, the image reconstruction block/section 13 joins the strip-like images which are the same in irradiation direction of the X-ray to generate a plurality of elongated images. In these elongated images, entire body images of the subject M different in the projection direction are seen.

The image reconstruction block/section 13 generates a tomographic image D by superimposing a plurality of elongated images. The principle of generating the tomographic image D is the same as the principle explained with reference to FIG. 2. Therefore, by simply superimposing a plurality of elongated images, a tomogram of the entire body of the subject at a reference cutting plane MA can be obtained. Further, by simply superimposing a plurality of elongated images, a tomogram of the entire body of the subject at an arbitrary cutting plane parallel to a reference cutting plane MA can be obtained. Thus, the image reconstruction section 13 generates a tomographic image obtained by cutting the subject M with a virtual plane as a composite image.

As explained above, according to the structure of Embodiment 3, an elongated image obtained by a slot image taking operation is generated, and a tomographic image D is generated from the elongated image. By performing such an image taking operation, a radiographic apparatus capable of obtaining a tomographic image taken in a wide range can be provided.

Embodiment 4

Figure 22:
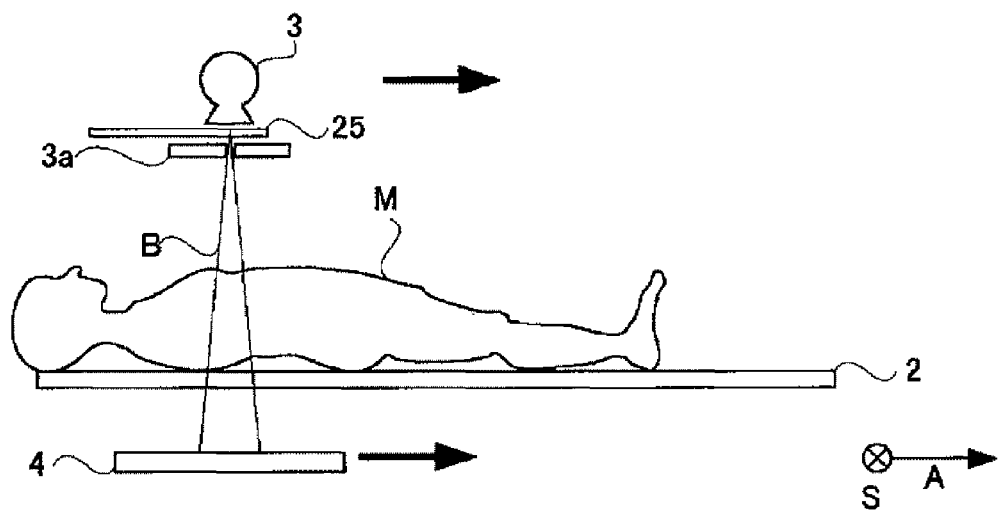
FIG. 22 is a schematic view explaining the operation of the radiographic apparatus according to Embodiment 4.
Figure 23:
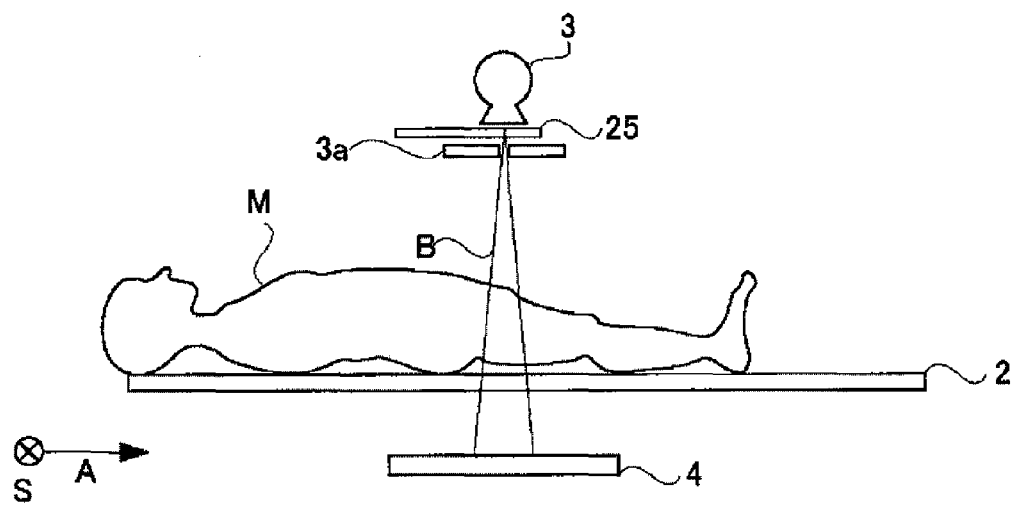
FIG. 23 is a schematic view explaining the operation of the radiographic apparatus according to Embodiment 4.
Figure 24:
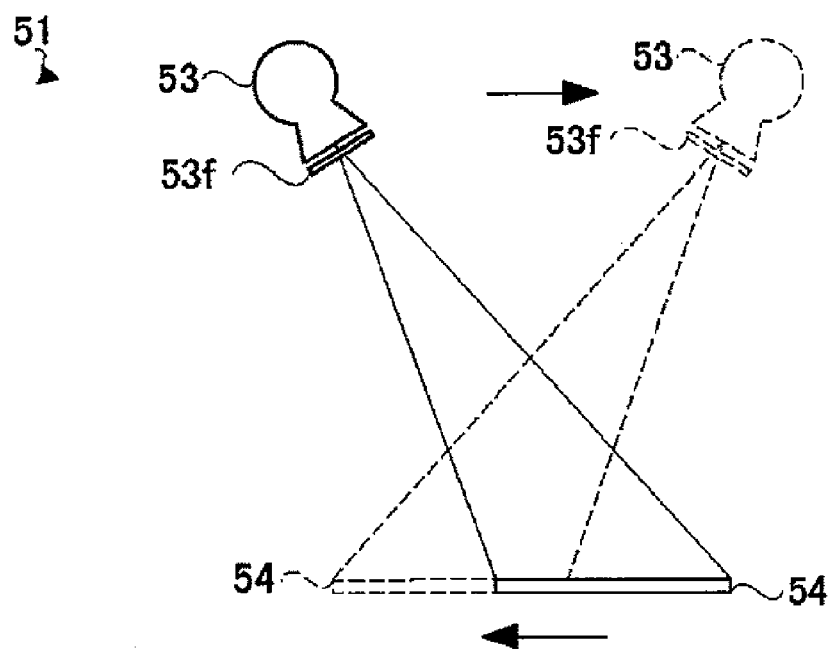
FIG. 24 is a schematic view explaining the structure of a radiographic apparatus according to the related art.
Figure 25:
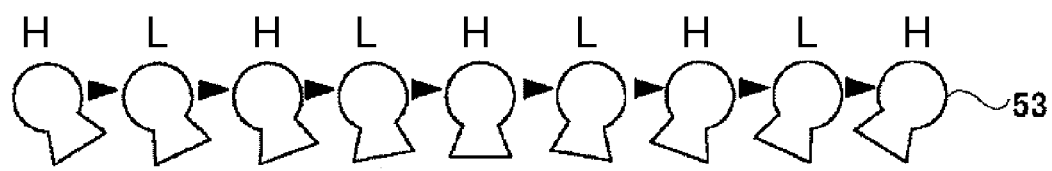
FIG. 25 is a schematic view explaining the structure of the radiographic apparatus according to the related art.

Next, an X-ray equipment according to Embodiment 4 will be explained with reference to FIGS. 22 and 23. In Embodiment 4, as shown in FIG. 22, it is structured such that tomographic images can be taken while moving the X-ray tube 3 and the FPD 4 in the body axis direction A of the subject M in a state in which the positional relationship of the X-ray tube 3 and the FPD 4 is kept. At this time, as the image taking method, a slot image taking method in Embodiment 2 is employed, and the image taking operation is performed while limiting the width of the X-ray in the body axis direction A by the collimator 3a. By doing so, it is possible to take a clear image over a wide range without being affected by scattered rays.

In Embodiment 4, it is structured such that an image taking operation under a high voltage condition and an image taking operation under a low voltage condition are performed alternately.

The structure of the X-ray equipment according to Embodiment 4 is the same as the functional block diagram shown in FIG. 1. Regarding FIG. 1, the structure of Embodiment 4 differs from that of Embodiment 1 in that the FPD 4 moves while following the X-ray tube 3 (see FIG. 22), the X-ray tube 3 does not tilt, and a tomographic image is not generated. Therefore, in Embodiment 4, the X-ray tilt mechanism 9, the X-ray tube tilt controller 10 and the image reconstruction block/section 13 shown in FIG. 1 are not always required.

<Operation of X-Ray Equipment>

The operation of the X-ray equipment according to Embodiment 4 is the same as the operation of the device according to Embodiment 1 explained with reference to FIG. 11. FIG. 22 shows a state immediately before initiation of the image taking operation under a high voltage condition. As shown in FIG. 22, the X-ray tube 3 and the FPD 4 are positioned at the head portion side of the subject M and move in one direction toward the toe side of the subject M while intermittently taking transparent images in a continuous manner. When the X-ray tube 3 and the FPD 4 reach the toe side of the subject M, the image taking operation terminates. The control of the X-ray tube 3 and the holder 25 in this image taking operation is the same as that of Embodiment 1, and therefore the explanation will be omitted. FIG. 23 shows the state immediately after completion of the image taking operation.

The image subtraction block/section 12 obtains a subtraction image by obtaining the difference between each of the transparent images P1 and its corresponding transparent image P2 in the image subtraction step S3. The transparent image P2 corresponding to the transparent image P1 denotes a transparent image P2 taken before and after taking the transparent image P1. At this time, the same number of subtraction images as the transparent images P1 are obtained. This subtraction image is an elongated shape extending in the body width direction S of the subject M.

In the image reconstruction step S4, the image reconstruction block/section 13 arranges the plurality of subtraction images in the body axis direction A of the subject M and joins them to thereby generate a composite image.

As explained above, in Embodiment 4, it is structured such that a subtraction image is taken in the form of a slot image taking operation. By obtaining a subtraction image with a slot image taking operation, it is possible to provide a radiographic apparatus capable of obtaining a clear subtraction image without being affected by scattered radioactive rays.

The present disclosure is not limited to the aforementioned structure, and can be modified, for example, as shown below.

(1) In FIG. 4 of the aforementioned Embodiment, the holder 25 is only equipped with a filter 25*f* for taking a subtraction image, but the present disclosure is not limited to this structure. For example, it can be configured such that a filter to be used for a purpose of taking an subtraction image is held in the hole 25*b* that no filter 25*f* is provided among the plurality of holes 25*b* formed in the holder 25. As explained above, if it is configured such that the type of filters 25*f* through which an X-ray passes can be changed by rotating the holder 25 by the holder rotation mechanism 21, changing of filters 25*f* can be performed in accordance with the purpose of the image taking operation. For example, when performing a spot image taking operation, an image taking operation can be performed by selecting a filter 25*f* appropriate to this image taking operation.

(2) In each Embodiment explained above, a subtraction image is generated and then a tomographic image D is generated, but the present disclosure is not limited to this structure. It can be configured such that a tomographic image D taken by a high voltage image taking operation and a tomographic image D taken by a low voltage image taking operation are generated, and thereafter the difference thereof is calculated to obtain a subtraction image. In the functional block diagram having such a structure, the position of the image subtraction block/section 12 and the position of the image reconstruction block/section 13 in FIG. 1 is replaced with each other.

(3) The aforementioned Embodiments are directed to medical apparatuses, but the present disclosure can also be applied to, e.g., industrial or nuclear power apparatuses.

(4) The X-ray in each Embodiment is one example of radioactive rays. Therefore, the present disclosure can also be applied to radioactive rays other than an X-ray.

The entire disclosure of Japanese Patent Application No. 2012-124602 filed on May 31, 2012, which describes certain features related to the present disclosure, is incorporated herein by reference in its entirety.

The terms and descriptions used herein are used only for explanatory purposes and the present invention is not limited to them. Accordingly, the present invention allows various design-changes falling within the claimed scope of the present invention.

While the present invention may be embodied in many different forms, a number of illustrative embodiments are described herein with the understanding that the present disclosure is to be considered as providing examples of the principles of the invention and such examples are not intended to limit the invention to embodiments described herein and/or illustrated herein.

For example, the present invention is not limited to the various embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive.

In this disclosure and during the prosecution of this application, the terminology "present invention" or "invention" is meant as a non-specific, general reference and may be used as a reference to one or more aspects within the present disclosure. The language present invention or invention should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features.

What is claimed is:

1. A radiographic apparatus comprising:
a radiation source that irradiates radiation toward a subject;
radiation source control means for controlling a voltage of the radiation source;
radiation source moving means for moving the radiation source with respect to the subject;
radiation source movement control means for controlling the radiation source moving means;
a filter having a high voltage region through which the radiation irradiated when the radiation source is in a high voltage state passes and a low voltage region through which the radiation irradiated when the radiation source is in a low voltage state passes;
a holder that moves in accordance with a movement of the radiation source and holds the filter at one of a plurality of holes provided in the holder;
holder rotation means for rotating the holder;
holder rotation control means for controlling the holder rotation means;
radiation detection means for detecting the radiation passed through the filter and the subject; and
image generation means for generating an image based on an output of the radiation detection means.

2. The radiographic apparatus as recited in claim 1, wherein the holder rotation means is configured to switch whether or not radiation irradiated from the radiation source passes through the filter, move the high voltage region of the filter to a position where the radiation passes through when the radiation source is in the high voltage state and move the low voltage region of the filter to a position where the radiation passes through when the radiation source is in the low voltage state.

3. The radiographic apparatus as recited in claim 1, wherein the holder rotation means moves one of regions of the filter to a position through which the radiation passes and then inverts a rotation direction of the holder when moving the other region to a position through which the radiation passes.

4. The radiographic apparatus as recited in claim 1,
wherein the filter is a filter for taking a subtraction image, and
wherein the radiographic apparatus further comprises:
image subtraction means for generating a subtraction image by obtaining a difference between an image continuously taken under a high voltage condition of the radiation source and an image continuously taken under a low voltage condition of the radiation source; and
image composing means for generating a composite image by composing the subtraction images.

5. The radiographic apparatus as recited in claim 4, wherein the holder includes a filter used for a purpose of taking an image other than a subtraction image, and wherein the holder rotation means rotates the holder to change a type of filter through which the radiation passes.

6. The radiographic apparatus as recited in claim 1, further comprising a collimator that limits an irradiation range of the radiation passed through the holder.

7. The radiographic apparatus as recited in claim 4, further comprising:
detector moving means for moving the radiation detection means with respect to the subject; and
detector movement control means for controlling the detector moving means,
wherein when the radiation source is moved, the radiation detection means is moved with respect to the subject.

8. The radiographic apparatus as recited in claim 7, wherein the image composing means generates a tomographic image to be obtained by cutting the subject with a virtual plane as the composite image.

9. The radiographic apparatus as recited in claim 8, wherein the image composing means arranges elongated subtraction images extending in a direction perpendicular to a moving direction of the radiation source and joins them to thereby generate the composite image.

10. The radiographic apparatus as recited in claim 4, wherein the image composing means divides the subtraction image into elongated strip-like images extending in a direction perpendicular to a moving direction of the radiation source and joins the strip-like images same in an irradiation direction of radiation to generate an intermediate image and generate a tomographic image to be obtained by cutting the subject with a virtual plane from the intermediate image as the composite image.

11. The radiographic apparatus as recited in claim 4, wherein the composite image generated by the image composing means is an image formed by arranging elongated subtraction images extending in a direction perpendicular to a moving direction of the radiation source in the moving direction of the radiation source and joining them, and wherein the radiation detection means does not move with respect to the subject during an image taking operation.

12. A radiographic apparatus comprising:
a radiation source configured to irradiate radiation toward a subject;
a radiation source controller configured to control a voltage of the radiation source;
a radiation source movement mechanism configured to move the radiation source with respect to the subject;
a radiation source movement controller configured to control the radiation source movement mechanism;
a filter having a high voltage region through which the radiation irradiated when the radiation source is in a high voltage state passes and a low voltage region through which the radiation irradiated when the radiation source is in a low voltage state passes;
a holder configured to move in accordance with a movement of the radiation source and holds the filter at one of a plurality of holes provided in the holder;
a holder moving device configured to move the holder;
a holder movement controller configured to control the holder moving device;
a radiation detector configured to detect the radiation passed through the filter and the subject; and
an image generation block configured to generate an image based on an output of the radiation detector.

13. The radiographic apparatus as recited in claim 12, further comprising:
an image subtraction block configured to generate a subtraction image by obtaining a difference between an image taken under a high voltage condition of the radiation source and an image taken under a low voltage condition of the radiation source; and
an image reconstruction block configured to reconstruct a tomographic image by reconstructing the subtraction images.

14. The radiographic apparatus as recited in claim 13, further comprising a collimator configured to limit an irradiation range of the radiation passed through the holder.

15. The radiographic apparatus as recited in claim 14, wherein the holder is arranged between the radiation source and the collimator in a manner such that the high voltage region of the filter and the low voltage region of the filter are replaceably positioned to a portion through which the radiation passes.

16. A method of obtaining images using a radiographic apparatus including a radiation source, a filter including first and second regions, and a radiation detector, the method comprising:

controlling a voltage used by the radiation source for irradiation;

controlling movement of the radiation source with respect to the subject;

irradiating radiation using the radiation source in one of a high voltage state or a low voltage state through the first region of the filter;

detecting, by the radiation detector, the radiation passed through the first region of the filter and the subject;

moving the filter using a holder that moves in accordance with a movement of the radiation source and which holds the filter at one of a plurality of holes provided in the holder;

after moving the filter, irradiating radiation using the radiation source in the other of the high voltage state or the low voltage state through the second region of the filter;

detecting, by the radiation detector, the radiation passed through the second region of the filter and the subject; and generating an image based on output from the radiation detector.

17. The method of claim 16, wherein the first region of the filter is horizontally adjacent to the second region of the filter.

18. The method of claim 17, wherein moving the filter includes moving a holder that holds the filter.

19. The method of claim 18, wherein moving the holder includes rotating the holder.

20. The method of claim 18, further comprising:

prior to the irradiating steps, placing the filter in an opening of the holder, the opening having a shape that accommodates the filter.

\* \* \* \* \*